(12) United States Patent
Furuya et al.

(10) Patent No.: US 7,914,967 B2
(45) Date of Patent: Mar. 29, 2011

(54) FLUORINE-CONTAINING COMPOUND, RESIST COMPOSITION FOR IMMERSION EXPOSURE, AND METHOD OF FORMING RESIST PATTERN

(75) Inventors: Sanae Furuya, Kawasaki (JP); Takayoshi Mori, Kawasaki (JP); Takahiro Dazai, Kawasaki (JP); Ryoichi Takasu, Kawasaki (JP); Tomoyuki Hirano, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 260 days.

(21) Appl. No.: 12/184,566

(22) Filed: Aug. 1, 2008

(65) Prior Publication Data
US 2009/0047602 A1  Feb. 19, 2009

(30) Foreign Application Priority Data

Aug. 3, 2007 (JP) ................ 2007-203177
Nov. 12, 2007 (JP) ................ 2007-293145
Mar. 26, 2008 (JP) ................ 2008-080695

(51) Int. Cl.
*G03F 7/00* (2006.01)
*G03F 7/004* (2006.01)

(52) U.S. Cl. .............. 430/270.1; 430/311; 430/905; 430/945

(58) Field of Classification Search ........... 430/270.1, 430/905, 945, 311
See application file for complete search history.

(56) References Cited

U.S. PATENT DOCUMENTS

| | | | |
|---|---|---|---|
| 5,773,191 A * | 6/1998 | Padmanaban et al. | 430/270.1 |
| 5,945,517 A | 8/1999 | Nitta et al. | |
| 6,005,137 A * | 12/1999 | Moore et al. | 560/139 |
| 6,153,733 A | 11/2000 | Yukawa et al. | |
| 6,362,379 B2 * | 3/2002 | Moore et al. | 568/676 |
| 6,423,467 B1 * | 7/2002 | Kawauchi et al. | 430/270.1 |
| 6,746,812 B2 * | 6/2004 | Watanabe et al. | 430/165 |

(Continued)

FOREIGN PATENT DOCUMENTS
EP  1835342 A2 *  9/2007
(Continued)

OTHER PUBLICATIONS

Gil et al., "First Microprocessors with Immersion Lithography", Proceedings of SPIE, vol. 5754, pp. 119-128, (2005).

(Continued)

*Primary Examiner* — Amanda C. Walke
(74) *Attorney, Agent, or Firm* — Knobbe, Martens, Olson & Bear, LLP

(57) ABSTRACT

A resist composition for immersion exposure including a base component (A) which exhibits changed solubility in an alkali developing solution under action of acid, an acid-generator component (B) which generates acid upon irradiation, and a fluorine-containing compound (C) having a group represented by general formula (c) shown below and containing at least one fluorine atom:

[Chemical Formula 1]

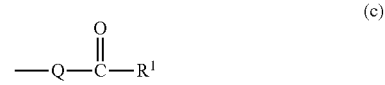

wherein Q represents a group in which one hydrogen atom has been removed from a monovalent hydrophilic group; and $R^1$ represents a hydrocarbon group of 2 or more carbon atoms which may have a fluorine atom.

11 Claims, 1 Drawing Sheet

U.S. PATENT DOCUMENTS

| | | | |
|---|---|---|---|
| 7,618,762 B2 * | 11/2009 | Kunita et al. | 430/138 |
| 2003/0232940 A1 | 12/2003 | Komoriya et al. | |
| 2003/0236369 A1 * | 12/2003 | Komoriya et al. | 526/246 |
| 2005/0019690 A1 * | 1/2005 | Kodama | 430/270.1 |
| 2006/0094817 A1 | 5/2006 | Harada et al. | |
| 2007/0134447 A1 * | 6/2007 | Kato | 428/1.31 |

FOREIGN PATENT DOCUMENTS

| | | |
|---|---|---|
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| KR | 10-2003-0076194 A | 9/2003 |
| KR | 10-2006-0052244 A | 5/2006 |
| WO | WO 2004/074242 A2 | 9/2004 |

OTHER PUBLICATIONS

Kodama et al., "Synthesis of Novel Fluoropolymer for 157 nm Photoresists by Cyclo-polymerization", Proceedings of SPIE, vol. 4690, pp. 76-83, (2002).

Office Action (Notice of Allowance) issued in counterpart Korean Patent Application No. 10-2008-0075642, dated Nov. 30, 2010.

* cited by examiner

FLUORINE-CONTAINING COMPOUND, RESIST COMPOSITION FOR IMMERSION EXPOSURE, AND METHOD OF FORMING RESIST PATTERN

TECHNICAL FIELD

The present invention relates to a fluorine-containing compound, a resist composition for immersion exposure (immersion lithography) including the fluorine-containing compound, and a method of forming a resist pattern using the resist composition for immersion exposure.

Priority is claimed on Japanese Patent Application No. 2007-203177, filed Aug. 3, 2007, Japanese Patent Application No. 2007-293145, filed Nov. 12, 2007, and Japanese Patent Application No. 2008-080695, filed Mar. 26, 2008, the contents of which are incorporated herein by reference.

BACKGROUND ART

In lithography techniques, fox example, a resist film composed of a resist material is formed on a substrate, and the resist film is subjected to selective exposure of radial rays such as light or electron beam though a mask having a predetermined pattern, followed by development, thereby forming a resist pattern having a predetermined shape on the resist film.

For miniaturization of semiconductor devices, shortening of the wavelength of the exposure light source, and increasing of the numerical aperture (NA) of the projector lens have progressed. Currently, exposure apparatuses in which an ArF excimer laser having a wavelength of 193 nm is used as an exposure light source and NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed solubility in an alkali developing solution under action of acid and an acid generator that generates acid upon exposure.

Currently, resins that contain structural its derived from (meth)acrylate esters within the main chain (acrylic resins) are now widely used as base resins for resists that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted using a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having Pious shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied, and water is mainly used as the immersion medium.

In recent years, fluorine-containing compounds have been attracting attention for their properties such as water repellency and transparency, and active research and development of fluorine-containing compounds have been conducted in various fields. For example, in the fields of resist materials, currently, an acid-labile group such as a methoxyethyl group, tert-butyl group or tert-butoxycarbonyl group is being introduced into a fluorine-containing polymeric compound, and the fluorine-containing polymeric compound is used as a base resin for a chemically amplified positive resist. However, when such a fluorine-containing polymeric compound is used as a base resin for a chemically amplified positive resist, disadvantages are caused in that a large amount of an out gas is generated, and resistance to a dry-etching gas (etching resistance) is unsatisfactory.

Recently, as a fluorine-containing polymeric compound exhibiting excellent etching resistance, a fluorine-containing polymeric compound having an acid-labile group containing a cyclic hydrocarbon group has been reported (see, for example, Non-Patent Document 2).

[Non-Patent Document 1] Proceedings of SPIE (U.S.), vol. 5754, pp. 119-128 (2005)

[Non-Patent Document 2] Proceedings of SPIE (U.S.), vol. 4690, pp. 76-83 (2002)

DISCLOSURE OF INVENTION

Means to Solve the Problems

In immersion exposure, it is required to use a resist material which exhibits not only general lithography properties (e.g., sensitivity, resolution, etching resistance and the like), but also properties suited for immersion lithography. For example, in immersion exposure, when the resist film comes in contact with the immersion medium, elution of a substance contained in the resist film into the immersion medium occurs. This elution of a substance causes phenomenons such as degeneration of the resist film and change in the refractive index of the immersion medium, thereby adversely affecting the lithography properties. The amount of the eluted substance is affected by the properties of the resist film surface (e.g., hydrophilicity, hydrophobicity, and the like). For example, by enhancing the hydrophobicity of die resist film surface, the elution of a substance can be reduced. Further, when the immersion medium is water, and immersion exposure is performed using a scanning-type immersion exposure apparatus as disclosed in Non-Patent Document 1, tracking ability of water with respect to the movement of the lens (hereafter, frequently referred to as "water tracking ability") is required. When the water tracking ability is low, the exposure speed becomes low, and as a result, there is a possibility that the productivity is adversely affected. It is presumed that the water tracking ability van be improved by enhancing the hydrophobicity of the resist film (rendering the resist film hydrophobic).

Thus, it is presumed that the above-described characteristic problems of immersion lithography such as reducing elution of a substance and improving the water tacking ability can be solved by enhancing the hydrophobicity of the resist film surface. However, when the resist film is simply rendered hydrophobic, lithography properties are adversely affected. For example, when the hydrophobicity of a resist film is enhanced, a problem occurs in that defects are likely to be generated in the resist film following alkali developing. Especially, in a positive resist composition, defects are likely to be generated unexposed portions. Here, defects refers to general abnormalities of a resist pattern, which are detected when observed from right above the developed resist pattern, using a surface defect detection equipment (trade name: "KLA") manufactured by KLA-TENCOR CORPORATION. Examples of these abnormalities include post-developing scum, foam, dust, bridges across different portions of the resist pattern, color irregularities, and foreign deposits.

It is presumed that the above-mentioned problems can be solved by a material which is hydrophobic dug immersion exposure, and becomes hydrophilic during developing. However, at present, a material exhibiting such properties is almost unknown.

The present invention takes the above circumstances into consideration, with an object of providing a novel fluorine-containing compound useful as an additive for a resist composition for immersion exposure, a resist composition for immersion exposure including the fluorine-containing compound, and a method of forming a resist pattern using the resist composition for immersion exposure.

Means to Solve the Problems

For solving the above-mentioned problems, the present invention employs the following aspects.

Specifically, a first aspect of the present invention is a resist composition for immersion exposure including a base component (A) which exhibits changed solubility in an alkali developing solution under action of acid, an acid-generator component (B) which generates acid upon irradiation, and a fluorine-containing compound (C) having a group represented by general formula (c) shown below and containing at least one fluorine atom:

[Chemical Formula 1]

(c)

wherein Q represents a group in which one hydrogen atom has been removed from a monovalent hydrophilic group; and $R^1$ represents a hydrocarbon group of 2 or more carbon atoms which may have a fluorine atom.

A second aspect of the present invention is a method of forming a resist pattern, including: applying a resist composition for immersion exposure according to the first aspect of the present invention to a substrate to form a resist film on the substrate; subjecting the resist film to immersion exposure; and developing the resist film to form a resist pattern.

A third aspect of the present invention is a fluorine-containing compound having a group represented by general formula (c) shown below and containing at least one fluorine atom:

[Chemical Formula 2]

(c)

wherein Q represents a group in which one hydrogen atom has been removed from a monovalent hydrophilic group; and $R^1$ represents a hydrocarbon group of 2 or more carbon atoms which may have a fluorine atom.

In the present description and claims, the term "structural unit" refers to a monomer unit that contributes to the formation of a resin component (polymer).

The term "exposure" is used as a general concept that includes irradiation with any form of radiation.

An "alkyl group" includes linear, branched or cyclic, monovalent saturated hydrocarbon, unless otherwise specified.

A "lower alkyl group" is an alkyl group of 1 to 5 carbon atoms.

Effect of the Invention

According to the present invention, there are provided a novel fluorine-containing compound useful as an additive for a resist composition for immersion exposure, a resist composition for immersion exposure including the fluorine-containing compound, and a method of forming a resist pattern using the resist composition for immersion exposure.

DESCRIPTION OF REFERENCE NUMERALS AND CHARACTERS

Figure 1:
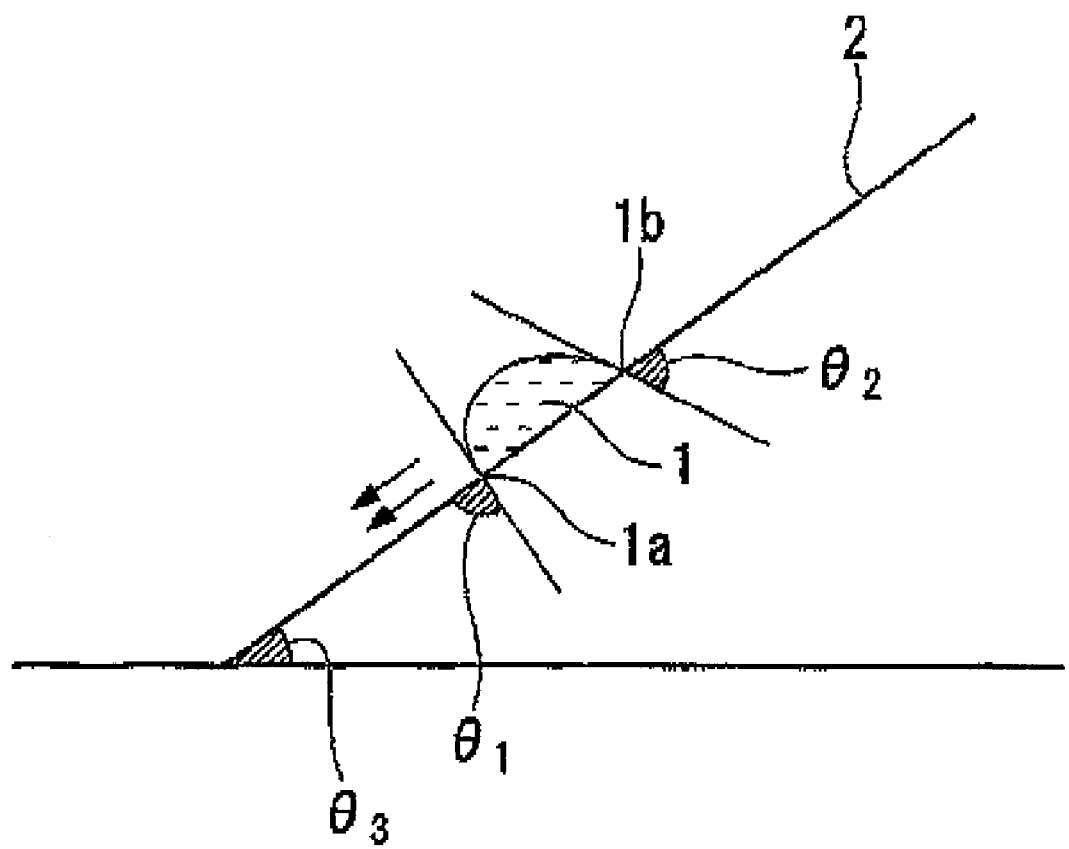
FIG. 1 is an explanatory diagram of advancing angle ($\theta_1$), receding angle ($\theta_2$) and sliding angle ($\theta_3$).

1 Droplet
1a Lower end
1b Upper end
2 Plane
($\theta_1$) Advancing angle
($\theta_2$) Receding angle
($\theta_3$) Sliding angle

BEST MODE FOR CARRYING OUT THE INVENTION

Fluorine-Containing Compound

Firstly, the fluorine containing compound of the present invention (hereafter, referred to as "fluorine-containing compound (C)") will be described. The fluorine-containing compound (C) is a component of the resist composition for immersion exposure according to the present invention, and is preferably used as an additive for a resist composition for immersion exposure.

The fluorine-containing compound (C) has a group represented by general formula (c) above, and contains at least one fluorine atom.

With respect to Q in general formula (c), the monovalent hydrophilic group may be any hydrophilic group having at least one hydrogen atom, and examples thereof include a hydroxyl group (—OH), a carboxy group (—C(=O)OH) and an amino group (—NH$_2$).

Q is a group in which one hydrogen atom has been removed from such a monovalent hydrophilic group. For example, when the monovalent hydrophilic group is —OH, Q is —O—. Alternatively when the monovalent hydrophilic group is —C(=O)OH, Q is —C(=O)O—. Furthermore, when the monovalent hydrophilic group is —NH$_2$. Q is —NH—.

As Q, —O— or —C(=O)O— is preferable, and —O— is particularly desirable.

$R^1$ represents a hydrocarbon group of 2 or more carbon atoms which may have a fluorine atom.

The fluorine-containing compound (C) has at least one fluorine atom in the structure thereof. Therefore, when no fluorine atom is included in a part of the fluorine-containing compound (C) excluding $R^1$ (e.g., $R^2$ in general formula (C-1) described below), $R^1$ is a fluorine-substituted hydrocarbon group. On the other hand, when a fluorine atom is included in a part of the fluorine-containing compound (C) excluding $R^1$, $R^1$ may be either an unsubstituted hydrocarbon group or a fluorine-substituted hydrocarbon group.

The hydrocarbon group for $R^1$ may be either an unsubstituted hydrocarbon group constituting of carbon atom and hydrogen atom, or a fluorine-substituted hydrocarbon group (fluorinated hydrocarbon group) in which a part or au of the hydrogen atoms within the above-mentioned unsubstituted hydrocarbon group is substituted with fluorine atoms.

The hydrocarbon group may be either an aliphatic hydrocarbon group, or an aromatic hydrocarbon group.

In the present description and claims, the term "aliphatic" is a relative concept used in relation to the term "aromatic", and defines a group or compound that has no aromaticity.

An aliphatic hydrocarbon group is a hydrocarbon group having no aromaticity. The aliphatic hydrocarbon group may be either saturated or unsaturated, but is preferably saturated. That is, as the aliphatic hydrocarbon group, an unsubstituted alkyl group or a fluorine-substituted alkyl group is preferable.

The unsubstituted all group may be any of linear, branched or cyclic. Alternatively, the unsubstituted alkyl group may be a combination of a linear or branched alkyl group and a cyclic alkyl group.

The unsubstituted linear alkyl group preferably has 2 to 10 carbon atoms, and more preferably 2 to 8. Specific examples include an ethyl group, n-propyl group, n-butyl group, n-pentyl group, n-hexyl group, n-heptyl group, n-octyl group, n-nonyl group and n-decanyl group.

The unsubstituted branched alkyl group preferably has 3 to 10 carbon atoms, and more preferably 3 to 8. As the branched alkyl group, a tertiary alkyl group is preferable, and a group represented by general formula (c-1) shown below is particularly desirable.

[Chemical Formula 3]

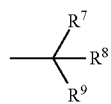

(c-1)

wherein each of $R^7$ to $R^9$ independently represents a linear alkyl group of 1 to 5 carbon atoms.

As the alkyl group for $R^7$ to $R^9$, an ethyl group or a methyl group is preferable, and a methyl group is particularly desirable.

As the unsubstituted cyclic alkyl group, for example, groups in which one hydrogen atom has been removed from a monocycloalkane or a polycycloalkane such as a bicycloalkane, tricycloalkane or tetracycloalkane can be mentioned. Specific examples include monocycloalkyl groups such as a cyclopentyl group and a cyclohexyl group; and polycycloalkyl groups such as an adamantyl group, a norbornyl group, an isobornyl group, a tricyclodecanyl group and a tetracyclododecanyl group.

Examples of the combination of a linear or branched alkyl group and a cyclic alkyl group include groups in which a cyclic alkyl group as a substituent is bonded to a linear or branched alkyl group, and groups in which a linear or branched alkyl group as a substituent is bonded to a cyclic alkyl group.

As the fluorine-substituted alkyl group, a group in which a part or all of the hydrogen atoms within the aforementioned unsubstituted hydrocarbon group is substituted with fluorine atoms can be exemplified.

The fluorine-substituted alkyl group may be either a group in which a pad of the hydrogen atoms within the aforementioned unsubstituted hydrocarbon group is substituted with fluorine atoms, or a group in which all of the hydrogen atoms within the aforementioned unsubstituted hydrocarbon group is substituted with fluorine atoms (i.e., a perfluoroalkyl group).

As the fluorine-substituted alkyl group for $R^1$, a linear or branched fluorine-substituted alkyl group is preferable, and a group represented by the formula: —$R^{41}$—$R^{42}$ (wherein $R^{41}$ represents an unsubstituted alkylene group of 1 to 9 carbon atoms, and $R^{42}$ represents a fluorine-substituted alkyl group of 1 to 9 carbon atoms, with the proviso that the total number of carbon atoms of $R^{41}$ and $R^{42}$ is no more than 10) is particularly desirable.

In the formula above, as $R^{41}$, a linear or branched alkylene group of 1 to 5 carbon atoms is preferable, and a methylene group, an ethylene group or a propylene group is particularly desirable.

As $R^{42}$, a linear or branched fluorine-substituted alkyl group is preferable, and a perfluoroalkyl group is particularly desirable. Among perfluoroalkyl groups, a trifluromethyl group and a tetrafluoroethyl group is preferable.

The structure of the fluorine-containing compound (C) of the present invention is not particularly limited, as long as it has a group represented by general formula (c) above, and contains a fluorine atom. For example, the fluorine-containing compound (C) may be either a polymeric compound (a polymer or copolymer) which has a group represented by general formula (c) above on the side chain thereof, or a low molecular weight compound (a non-polymer).

When the fluorine-containing compound (C) is a low molecular weight compound, the fluorine-containing compound (C) is preferably a compound represented by general formula (C-1) shown below (hereafter, referred to as "compound (C-1)").

When the fluorine-containing compound (C) is a polymeric compound, the fluorine-containing compound (C) is preferably a polymeric compound having a structural unit represented by general formula (c1-1-1), (c1-1-2), (c1-1-3) or (c1-1-4) shown below hereafter, referred to as "polymeric compound (C1)").

[Chemical Formula 4]

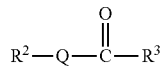
(C-1)

wherein Q represents a group in which one hydrogen atom has been removed from a monovalent hydrophilic group; $R^2$ represents an aromatic cyclic group-containing organic group which may have a fluorine atom, and $R^3$ represents a hydrocarbon group of 2 or more carbon atoms which may have a fluorine atom, with the proviso that at least one of $R^2$ and $R^3$ has a fluorine atom.

[Chemical Formula 5]

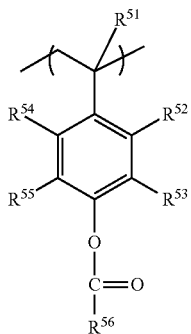
(c1-1-1)

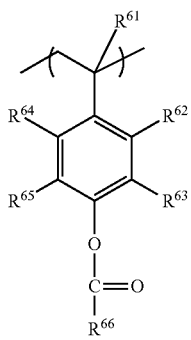
(c1-1-2)

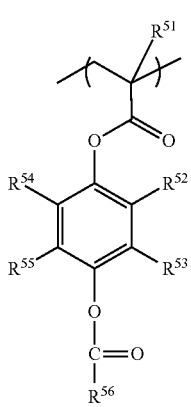
(c1-1-3)

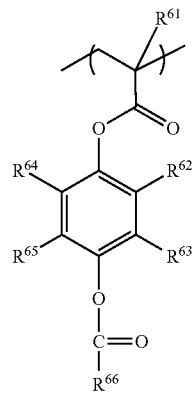
(c1-1-4)

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represents a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

Herebelow, the compound (C-1) and the polymeric compound (C1) will be described in detail.

[Compound (C-1)]

In general formula (C-1), the organic group for $R^2$ may be either constituted of only the aromatic cyclic group, or constituted of the aromatic cyclic group and a group other than the aromatic cyclic group.

As the organic group for $R^2$, a group in which one hydrogen atom has been removed from an aromatic hydrocarbon ring having a substituent is preferable.

The ring skeleton of the aromatic hydrocarbon ring preferably has 6 to 15 carbon atoms, and examples thereof include a benzene ring, a napthalene ring, a phenanthrene ring and an anthracene ring. Among these, a benzene zing is particularly desirable.

The number of substituents of the aromatic hydrocarbon ring may be either 1 or 2 or more, and is preferably 1.

As a preferable substituent for the aromatic hydrocarbon ring, a substituent containing a polymerizable group can be exemplified.

The polymerizable group is a group which renders a compound having the polymerizable group polymerizable by radical polymerization or the like. As the polymerizable group, a polymerizable group typically use in a monomer can be exemplified, and specific examples include groups having an ethylenic unsaturated double bond.

Examples of groups having an ethylenic unsaturated double bond include a group represented by the formula: $CH_2=C(R^{03})-(CH_2)_b-$; and a group represented by the formula: $CH_2=C(R^{03})-C(=O)-O-$. Among these, a group represented by the formula: $CH_2=C(R^{03})-(CH_2)_b-$, and a group represented by the formula: $CH_2=C(R^{03})-C(=O)-O-$ are preferable.

In the formulas above, $R^{03}$ represents a hydrogen atom, a lower alkyl group or a halogenated lower alkyl group.

Specific examples of lower alkyl groups for $R^{03}$ include linear or branched alkyl groups such as a methyl group, ethyl group, propyl group, isopropyl group, n-butyl group, isobutyl group, tert-butyl group, pentyl group, isopentyl group, and neopentyl group.

Specific examples of halogenated lower alkyl groups for $R^{03}$ include groups in which a part or all of the hydrogen atoms of the aforementioned lower alkyl group are substituted with halogen atoms. Examples of halogen atoms include fluorine atoms, chlorine atoms, bromine atoms and iodine atoms, and fluorine atoms are particularly desirable.

As $R^{03}$, a hydrogen atom, a lower alkyl group or a fluorinated lower alkyl group is preferable, and a hydrogen atom or a methyl group is more preferable.

b represents an integer of 0 to 2, preferably 0 or 1, and most preferably 0.

The substituent containing a polymerizable group may be either a group constituted of only the polymerizable group, or a group constituted of the polymerizable group and a group other than the polymerizable group.

As the group constituted of the polymerizable group and a group other than the polymerizable group, for example, a group constituted of the aforementioned polymerizable group and a divalent linking group can be exemplified. Examples of the divalent linking group include a hydrocarbon group and a group containing a hetero atom. As the hydrocarbon group, the same as those exemplified above as the alkylene group for $R^{01}$ can be mentioned. A hetero atom is an atom other than a carbon atom and a hydrogen atom, and examples thereof include an oxygen atom, a nitrogen atom, a sulfur atom and a halogen atom. Examples of groups containing a hetero atom include —O—, —C(=O)—, —C(=O)—O—, —NH—, —NR$^{04}$— (wherein $R^{04}$ represents an alkyl group), —NH—C(=O)—, =N—, and a combination of any of these groups with a divalent hydrocarbon group.

In the present invention as the organic group for $R^2$, a group in which one hydrogen atom has been removed from an aromatic hydrocarbon ring having a substituent containing a polymerizable group. Especially, as the substituent containing a polymerizable group, a group represented by general formula CH$_2$=C(R$^{03}$)—(CH$_2$)$_b$— or a group represented by general formula CH$_2$=C(R$^{03}$)—C(=O)—O— is preferable. In general formulas above, $R^{03}$ and b are as defined above.

Further, with respect to $R^2$, examples of substituents for the aforementioned aromatic hydrocarbon ring, which is other than the aforementioned substituents containing a polymerizable group, include a halogen atom, an alkyl group, an alkoxy group, a halogenated lower alkyl group and an oxygen atom (=O).

In the present invention, it is preferable that the aforementioned aromatic hydrocarbon ring has at least one fluorine atom as a substituent. In such a case, the fluorination ratio of the aromatic hydrocarbon ring, i.e., percentage (%) of the number of fluorine atoms, based on the total number of fluorine atoms and hydrogen atoms contained in the aromatic hydrocarbon ring, is preferably 10 to 100%, more preferably 50 to 100%, and most preferably 100%. That is, it is particularly desirable that all of the hydrogen atoms within the aromatic hydrocarbon ring are substituted with fluorine atoms.

As $R^3$, the same as the aforementioned $R^1$ can be exemplified.

The compound (C-1) has at least one fluorine atom in the structure thereof.

Therefore, when $R^2$ has no fluorine atoms, $R^3$ has a fluorine atom. When $R^2$ has a fluorine atom, $R^3$ may or may not have a fluorine atom. When $R^3$ has no fluorine atoms, $R^2$ has a fluorine atom. When $R^3$ has a fluorine atom, $R^2$ may or may not have a fluorine atom.

As the compound (C-1), a compound represented by general formula (C-1-1), (C-1-2), (C-1-3) or (C-1-4) shown below is particularly desirable.

[Chemical Formula 6]

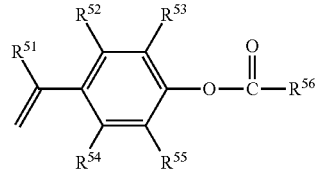
(C-1-1)

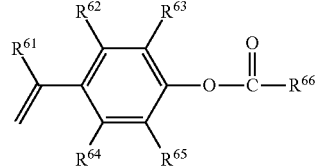
(C-1-2)

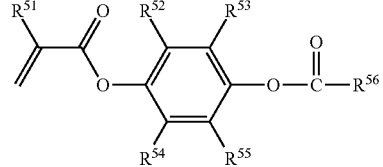
(C-1-3)

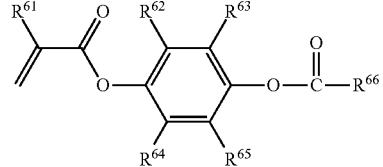
(C-1-4)

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represent a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

As $R^{51}$, the same as the aforementioned $R^{03}$ cm be exemplified. $R^{51}$ is preferably a hydrogen atom, a lower alkyl group or a fluorinated lower alkyl group, and more preferably a hydrogen atom or a methyl group.

Each of $R^{52}$ to $R^{55}$ independently represents a hydrogen atom or a fluorine atom, with the proviso that at least one of $R^{52}$ to $R^{55}$ represents a fluorine atom. In consideration of ease in production, it is particularly desirable that all of $R^{52}$ to $R^{55}$ are fluorine atoms.

As $R^{56}$, the same as the aforementioned $R^3$ can be exemplified. Among the examples, an unsubstituted or fluorine-substituted branched alkyl group is preferable, and an unsubstituted or fluorine-substituted tertiary alkyl group or a group represented by the aforementioned formula —R$^{41}$—R$^{42}$ is more preferable. As the unsubstituted or fluorine-substituted tertiary alkyl group, a group represented by general formula (c-1) shown above is particularly desirable.

As $R^{61}$, the same as the aforementioned $R^{51}$ can be exemplified.

Each of $R^{62}$ to $R^{65}$ independently represents a hydrogen atom or a fluorine atom. In consideration of ease in production, it is particularly desirable that all of $R^{62}$ to $R^{65}$ be either fluorine atoms or hydrogen atoms.

As $R^{66}$, among the hydrocarbon groups of 2 or more carbon atoms for $R^{56}$ which may have a fluorine atom, those which have a fluorine atom can be exemplified.

Among these, as the compound (C-1), a compound represented by general formula (C-1-1) or (C-1-4) above is preferable, and a compound represented by genera formula (C-1-11), (C-1-12), (C-1-41) or (C-1-42) shown below is more preferable.

[Chemical Formula 7]

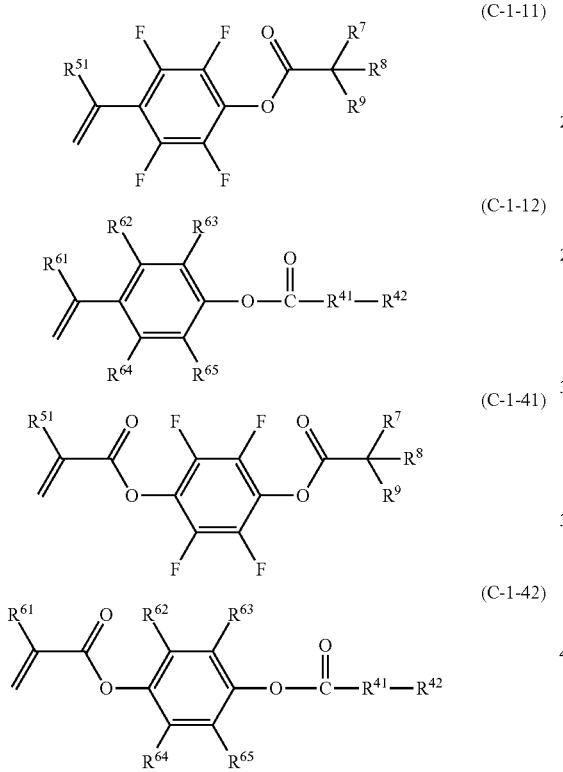

wherein $R^{51}$, $R^7$ to $R^9$, $R^{61}$ to $R^{65}$, $R^{41}$ and $R^{42}$ are as defined above.

The compound (C-1) per se win be preferably used as an additive for a resist composition.

Alternatively, when the compound (C-1) is a compound having a polymerizable group, such as a compound represented by general formula (C-1-1), (C-1-2), (C-1-3) or (C-1-4) above, the compound (C-1) may be polymerized alone or copolymerized with another polymerizable compound to obtain a polymeric compound. Such a polymeric compound, like the compound (C-1), can be preferably used as an additive for a resist composition for immersion exposure.

The compound represented by general formula (C-1-1), (C-1-2), (C-1-3) or (C-1-4) above can be used for producing the polymeric compound (C1) described below.

[Polymeric Compound (C1)]

The polymeric compound (C1) has a structural unit represented by general formula (c1-1-1), (c1-1-2), (c1-1-3) or (c1-1-4) above (hereafter, referred to as "structural unit (c1)").

In general formulas (c1-1-1) to (c1-1-4), $R^{51}$ to $R^{56}$ and $R^{61}$ to $R^{66}$ are respectively as defined for $R^{51}$ to $R^{56}$ and $R^{61}$ to $R^{66}$ in general formulas (C-1-1) to (C-1-4) above.

As the structural unit (c1), it is preferable that the polymeric compound (C1) has a structural unit represented by general formula (c1-1-1) or (c1-1-2) above, and more preferably a structural unit represented by general formula (c1-1-1) above. It is particularly desirable that the polymeric compound (C1) has a structural unit represented by general formula (c1-1-11) or (c1-1-12) shown below.

[Chemical Formula 8]

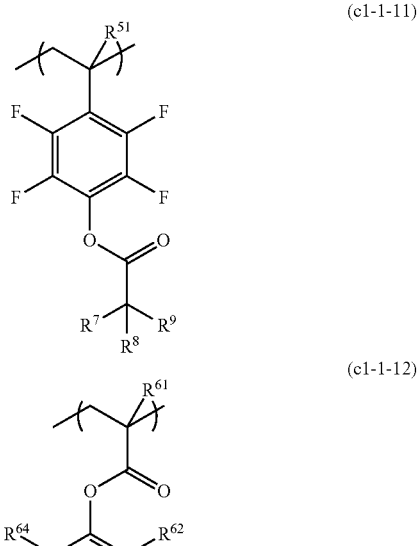

wherein $R^{51}$, $R^7$ to $R^9$, $R^{61}$ to $R^{65}$, $R^{41}$ and $R^{42}$ are as defined above.

In the polymeric compound (C1), the amount of the structural unit (c1) based on the combined total of all structural units constituting the polymeric compound (C1) is preferably 30 to 100 mol %, more preferably 50 to 100 mol %, and still more preferably 60 to 100 mol %.

The polymeric compound (C1) may also have a structural unit which is other the above-mentioned structural unit (c1), as long as the effects of the present invention are not impaired. As such a structural unit, there is no particular limitation, although a structural unit derived from a compound copolymerizable with a compound represented by one of general formulas (C-1-1) to (C-1-4) is preferable. Specific examples of such a structural unit include the structural units (a1) to (a4) which a resin component (A1) may have, described below in connection with the resist composition for immersion expose; a structural unit derived from hydroxystyrene; and a structural unit derived from styrene. Among these, a structural unit (a1) is particularly desirable.

The weight average molecular weight (Mw) (the polystyrene equivalent value determined by gel permeation chromatography (GPC)) of the polymeric compound (C1) is not particularly limited, but is preferably 2,000 to 50,000, more preferably 3,000 to 30,000, and most preferably 5,000 to 20,000. By making the weight average molecular weight no more than the upper limit of the above-mentioned range, the polymeric compound (C1) exhibits satisfactory solubility in a resist solvent when used for a resist. On the other hand, by making the weight average molecular weight at least as large as the lower limit of the above-mentioned range, dry etching resistance and cross-sectional shape of the resist pattern becomes satisfactory.

Further, the dispersity (Mw/Mm) is preferably 1.0 to 5.0, more preferably 1.0 to 3.0, and most preferably 1.2 to 2.5. Here, Mn is the number average molecular weight.

The polymeric compound (C1) can be preferably used as an additive for a resist composition for immersion exposure.

[Production Method of Fluorine-Containing Compound (C)]

The fluorine-containing compound (C) of the present invention can be produced by, for example, introducing a group represented by the formula —C(=O)—R$^1$ (wherein R$^1$ is as defined above) into the hydrophilic group of a compound having a hydrophilic group represented by the formula -QH (wherein Q is as defined above).

The introduction of the group represented by the formula —C(=O)—R$^1$ can be conducted by a conventional method. For example, taking example of a compound (C-1) represented by general formula (C-1) above, a compound represented by general formula (I) shown below (hereafter referred to as "compound (I)") can be reacted with a compound represented by general formula (II) shown below (hereafter, referred to as "compound (II)"), thereby obtaining the compound (C-1).

[Chemical Formula 9]

wherein R$^2$, Q and R$^3$ are respectively as defined for R$^2$, Q and R$^3$ general formula (C-1) above, and X$^h$ represents a halogen atom or a hydroxyl group.

As the halogen atom for X$^h$, a bromine atom, a chlorine atom, an iodine atom and a fluorine atom can be exemplified. As X$^h$, in terms of reactivity, a bromine atom or a chlorine atom is preferable, and a chlorine atom is particularly desirable.

The method for reacting the compound (I) with the compound (II) is not particularly limited. For example, the compound (I) can be contacted with the compound (II) in a reaction solvent in the presence of a base. In this method, when X$^h$ is a halogen atom, for example, in the presence of a base, the compound (II) can be added to a solution obtained by dissolving the compound (I) in a reaction solvent. On the other hand, when X$^h$ is a hydroxyl group, for example, in the presence of a base and a condensing agent, the compound (I) can be added to a solution obtained by dissolving the compound (II) in a reaction solvent, thereby effecting a reaction (condensation reaction) between the compound (I) and the compound (II). Alternatively, when X$^h$ is a hydroxyl group, for example, in the presence of an acid, the compound (I) can be added to a solution obtained by dissolving the compound (II) in a reaction solvent, thereby effecting a reaction (condensation reaction) between the compound (I) and the compound (II).

As the compound (I) and the compound (II), commercially available compounds can be used. Alternatively, the compound (I) and the compound (II) may be synthesized.

As the reaction solvent, any solvent capable of dissolving the compound (I) and the compound (II) (which are raw materials) can be used. Specific examples include tetrahydrofuran (THF), acetone, dimethylformamide (DMF), dimethylacetamide, dimethylsulfoxide (DMSO) and acetonitrile.

Examples of the base include organic bases such as triethylamine, 4-dimethylaminopyridine (DMAP) and pyridine; and inorganic bases such as sodium hydride, K$_2$CO$_3$ and Cs$_2$CO$_3$.

As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids may be used alone, or in a combination of two or more.

Examples of the condensing agent include carbodiimide reagents such as ethydiisopropylaminocarbodiimide hydrochloride (EDCl), dicyclohexylcarboxyimide (DCC), diisopropylcarbodiimide and carbodiimidazole; tetraethyl pyrophosphate; and benzothiazole-N-hydroxytrisdimethylaminophosphonium hexafluorophosphide (Bop reagent).

The amount of the compound (II) added is preferably 1 to 3 times the molar amount of the compound (I), more preferably 1 to 2 times the molar amount of the compound (I).

The reaction temperature is preferably –20 to 40° C., more preferably 0 to 30° C.

The reaction time varies, depending on the reactivity of the compound (I) and the compound (II), the reaction temperature, and the like. However, in general, the reaction time is preferably 30 to 240 minutes, more preferably 60 to 180 minutes.

Further, when the fluorine-containing compound (C) is a polymeric compound, the fluorine-containing compound (C) can be obtained, for example, by a conventional radical polymerization or the like of the monomers corresponding with each of the desired structural units (e.g., a compound represented by one of general formulas (C-1-1) to (C-1-4)), using a radical polymerization initiator such as azobisisobutyronitrile (AIBN).

Alternatively, as described above, the fluorine-containing compound (C) can be obtained by introducing a group represented by the formula —C(=O)—R$^1$ (wherein R$^1$ is as defined above) into the hydrophilic group of a compound having a hydrophilic group represented by the formula -QH (wherein Q is as defined above) (e.g., a hydroxystyrene-based resin such as polyhydroxystyrene, an acrylic acid, or the like).

The above-described fluorine-containing compound (C) of the present invention is a novel compound which was conventionally unknown.

The fluorine-containing compound (C) can be preferably used as an additive for a resist composition, and a resist composition having the fluorine-containing compound (C) is suitable for immersion exposure.

The resist composition to which the fluorine-containing compound (C) is added is not particularly limited, as long as it is suitable for immersion exposure, although a chemically amplified resist composition containing a base component which exhibits changed solubility in an alkali developing solution under action of acid and an acid-generator component which generates acid upon irradiation is preferable.

The fluorine-containing compound (C) is particularly suitable for the resist composition for immersion exposure according to the present invention, which is described below.

<<Resist Composition for Immersion Exposure>>

The resist composition for immersion exposure according to the present invention includes a base component (A) which exhibits changed solubility in an alkali developing solution under action of acid (hereafter, referred to as "component (A)"), an acid-generator component (B) which generates acid upon irradiation (hereafter, referred to as "component (B)"), and a fluorine-containing compound (C) having a group represented by general formula (c) above and containing at least one fluorine atom (hereafter, referred to as "component (C)").

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, frequently referred to as low molecular weight compounds) and high molecular weight resins (polymeric materials) having a molecular weight of 2,000 or more. Generally, as the aforementioned low molecular weight compound, a non-polymer is used. With respect to the aforementioned resin polymer or copolymer), the molecular weight is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight material which exhibits changed solubility in an alkali developing solution under action of acid may be used.

When the resist composition for immersion exposure according to the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the crosslinked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 pas by weight, relative to 100 parts by weight of the alkali-soluble resin.

When the resist composition of the present invention is a positive resist composition, as the component (A), a base component which exhibits increased solubility in an alkali developing solution by action of acid is used. The component (A) is insoluble in an alkali developing solution prior to exposure, and when acid is generated from the component (B) upon exposure, the solubility thereof in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which exhibits increased solubility in an alkali developing solution under action of acid (hereafter, referred to as "component (A1)"), a low molecular weight compound (A2) which exhibits increased solubility in an alkali developing solution under action of acid (hereafter, referred to as "component (A2)"), or a mixture of the component (A1) and the component (A2).

[Component (A1)]

As the component (A1), a resin component (base resin) typically used as a base component for a chemically amplified resist composition van be used alone, or two or more of such resin components can be mixed together.

In the present invention, it is preferable that the component (A1) include a structural unit derived from an acylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the a position, and acrylate esters having a substituent (an atom other than a hydrogen atom or a group) bonded to the carbon atom on the α-position. As the substituent a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1)

As the acid-dissociable, dissolution-inhibiting group in the structural unit (a1), any of the groups that have been proposed as acid dissociable, dissolution inhibiting groups for the base resins of chemically amplified resist can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution.

Generally, groups at form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group at has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (═O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be exemplified. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclodecanyl group, and a branched alkylene group having a tertiary carbon atom bonded thereto, as the groups bonded to the oxygen atom of the carbonyl group (—C(O)—O—) within the structural units represented by general formulas (a1″-1) to (a1″-6) shown below, can be exemplified.

[Chemcial Formula 10]

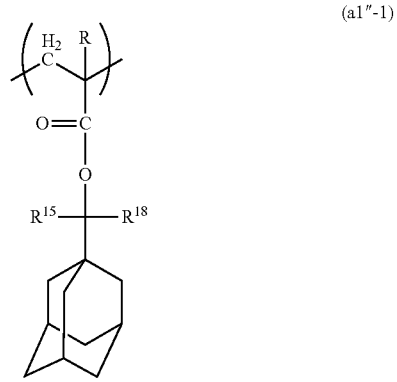

(a1″-1)

(a1″-2) 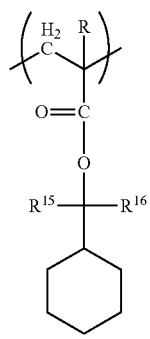

(a1″-3) 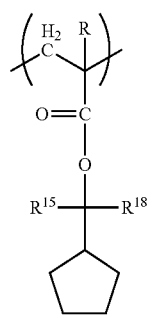

(a1″-4) 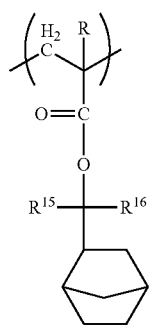

(a1″-5) 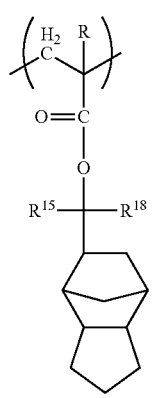

(a1″-6) 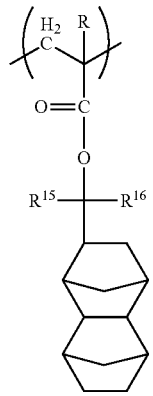

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 11]

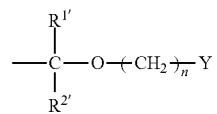

(p1)

wherein $R^{1\prime}$ and $R^{2\prime}$ each independently represents a hydrogen atom or a lower alkyl group, n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same as the lower alkyl groups for R above can be exemplified. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 12]

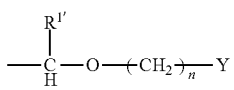

(p1-1)

wherein $R^{1\prime}$, n and Y are as defined above.

As the lower alkyl group for Y, the same as the lower alkyl groups for R above can be exemplified.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be exemplified.

Further, as the acetal-type, acid dissociable, dissolution inhibiting group, groups represented by general formula (p2) shown below can also be exemplified.

[Chemical Formula 13]

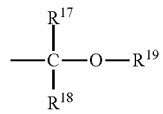

(p 2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the teal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be exemplified. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 14]

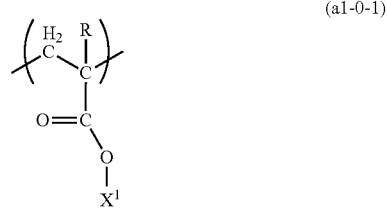

(a1-0-1)

wherein R represents a hydrogen atom, a lower alkyl group or a halogenated lower alkyl group; and $X^1$ represents a acid dissociable, dissolution inhibiting group.

[Chemical Formula 15]

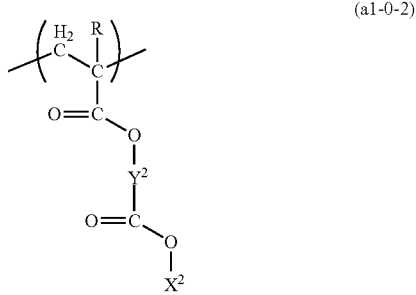

(a1-0-2)

wherein R represents a hydrogen atom, a lower alkyl group or a halogenated lower alkyl group; $X^2$ represents an acid dissociable, dissolution inhibiting group; and $Y^2$ represents a alkylene group or an aliphatic cyclic group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1).

$Y^2$ is preferably an alkylene group of 1 to 10 carbon atoms or a divalent aliphatic cyclic group. As the aliphatic cyclic group, the same as those exemplified above in connection with the explanation of "aliphatic cyclic group" can be used, except that two hydrogen atoms have been removed therefrom.

When $Y^2$ represents an alkylene group of 1 to 10 carbon atoms, it is more preferable that the number of carbons is 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

Specific examples of the structural unit (a1) include structural units represented by general formulas (a1-1) to (a1-4) shown below.

[Chemical Formula 16]

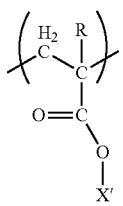

(a1-1)

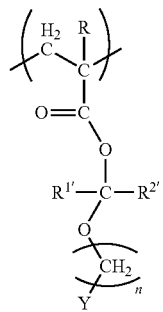

(a1-2)

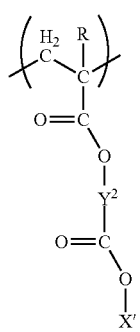

(a1-3)

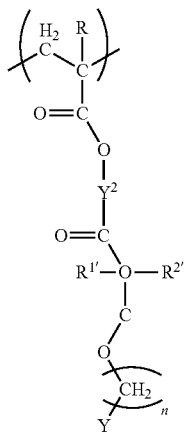

(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1'}$ and $R^{2'}$ each independently represents a hydrogen atom or a lower alkyl group of 1 to 5 carbon atoms.

Examples of the tertiary alkyl ester-type acid dissociable, dissolution inhibiting group for X' are the same as the above-exemplified tertiary alkyl ester-type acid dissociable, dissolution inhibiting groups for $X^1$.

As $R^{1'}$, $R^{2'}$, n and Y, the same as $R^{1'}$, $R^{2'}$, n and Y defined for general formula (p1) described above in connection with the "acetal-type acid dissociable, dissolution inhibiting group" may be exemplified.

As $Y^2$, the same as $Y^2$ defined for general formula (a1-0-2) above may be exemplified.

Specific examples of structural units represented by general formula (a1-1) to (a1-4) are shown below.

[Chemical Formula 17]

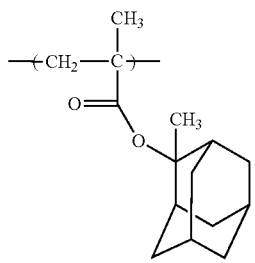

(a1-1-1)

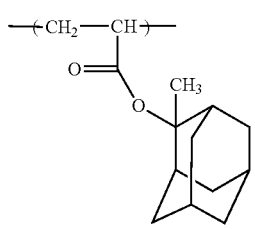

(a1-1-2)

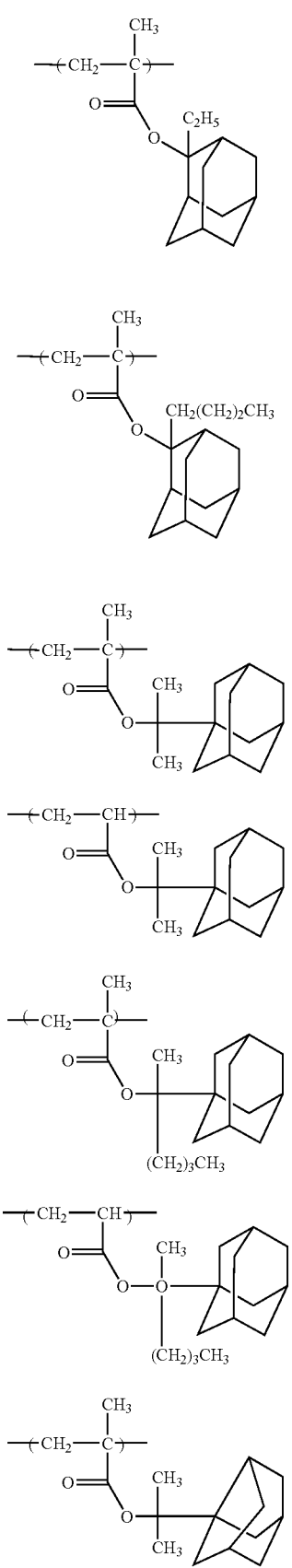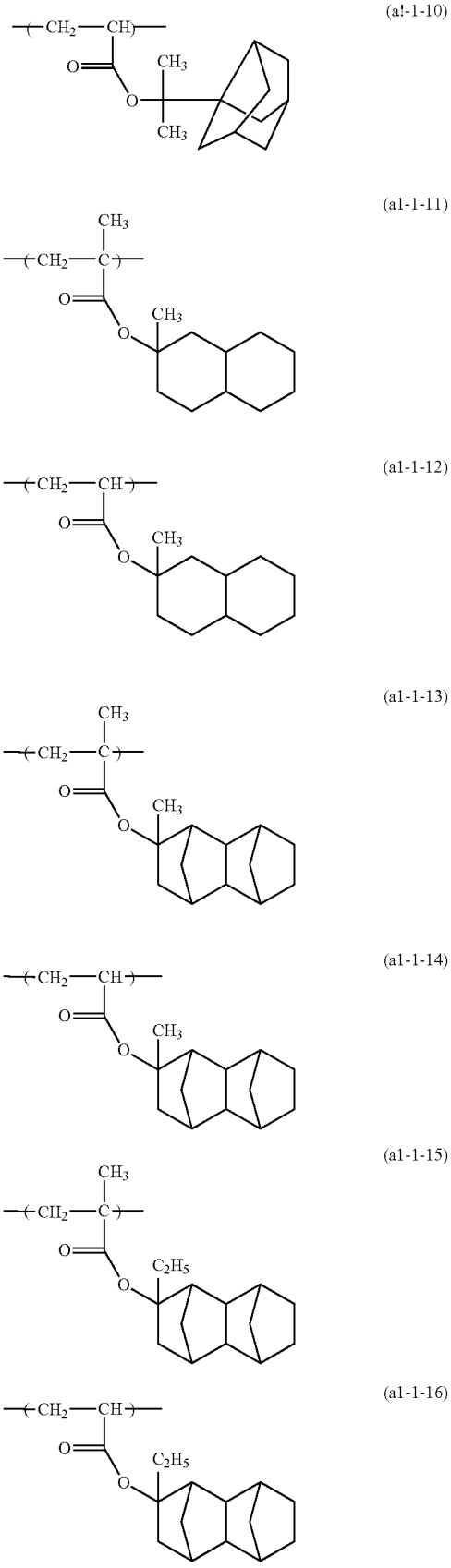

[Chemical Formula 18]

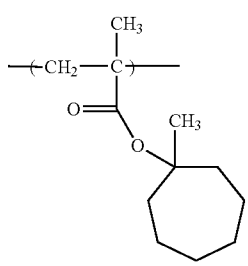 (a1-1-30)
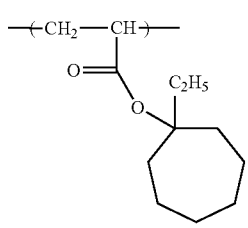 (a1-1-31)
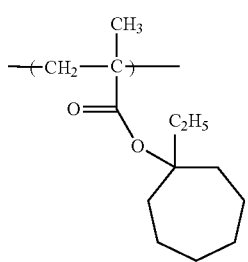 (a1-1-32)
[Chemical Formula 19]
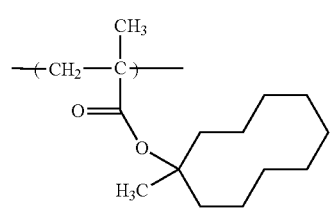 (a1-1-33)
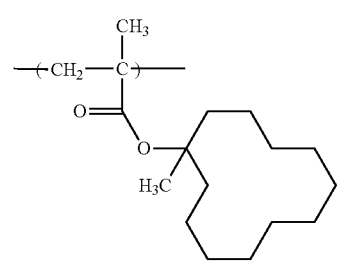 (a-1-34)
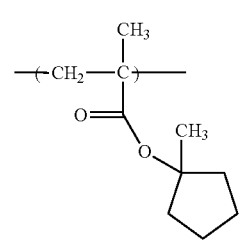 (a1-1-35)
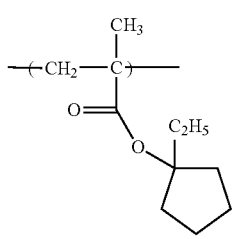 (a1-1-36)
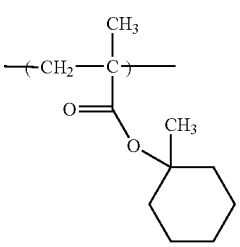 (a1-1-37)
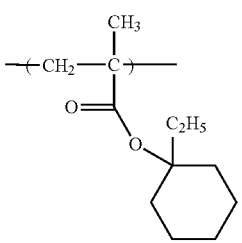 (a1-1-38)
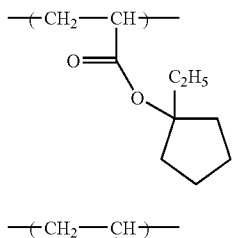 (a1-1-39)
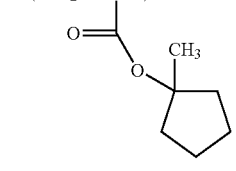 (a1-1-40)
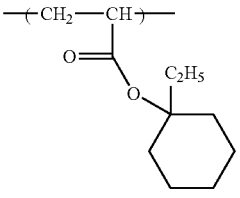 (a1-1-41)
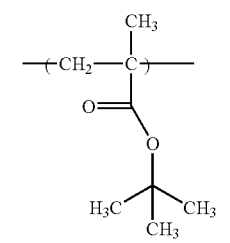 (a1-1-42)

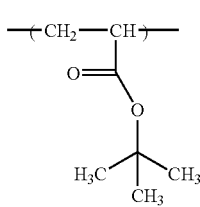 (a1-1-43)
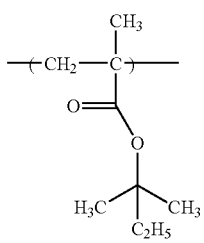 (a1-1-44)
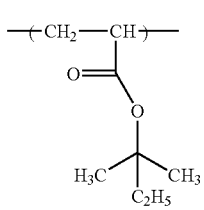 (a1-1-45)
[Chemical Formula 20]
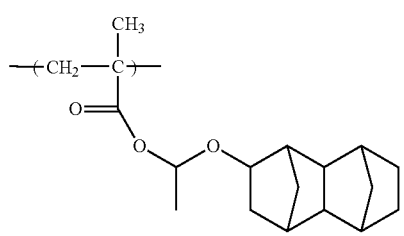 (a1-2-1)
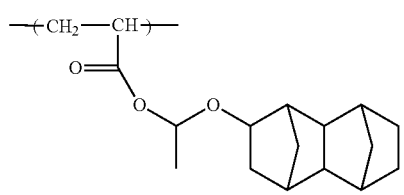 (a1-2-2)
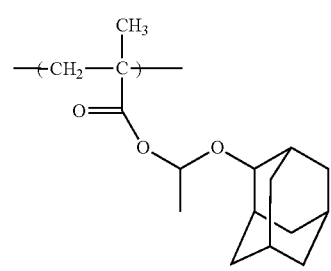 (a1-2-3)
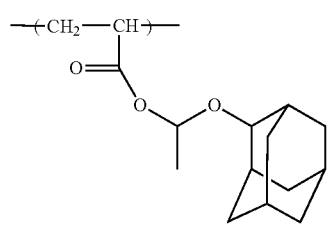 (a1-2-4)
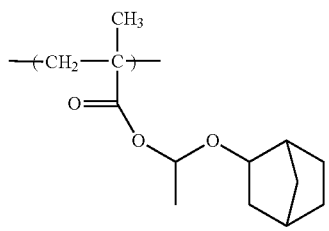 (a1-2-5)
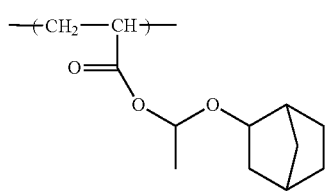 (a1-2-6)
[Chemical Formula 21]
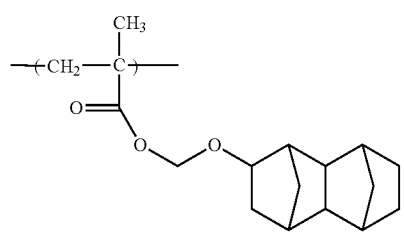 (a1-2-7)
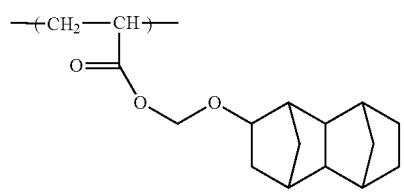 (a1-2-8)
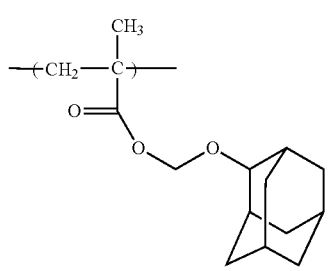 (a1-2-9)
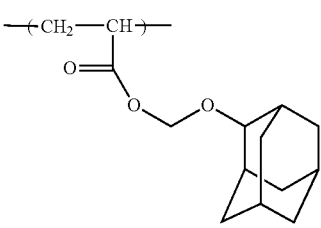 (a1-2-10)
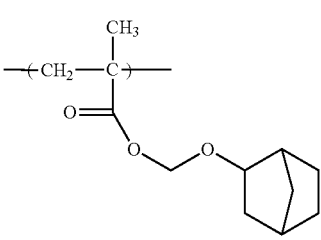 (a1-2-11)

(a1-2-12) 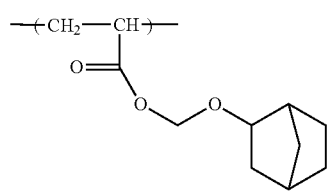
(a1-2-13) 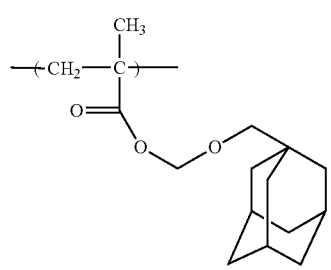
(a1-2-14) 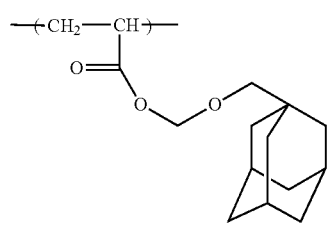
(a1-2-15) 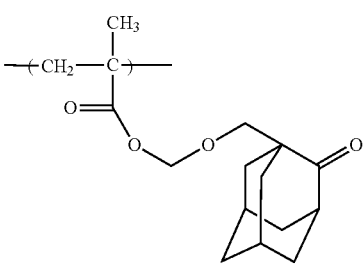
(a1-2-16) 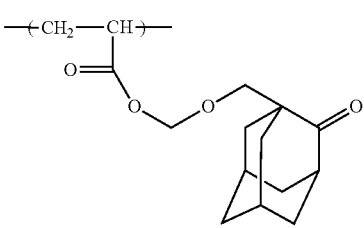
(a1-2-17) 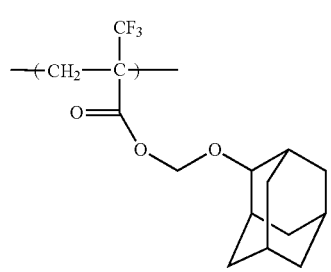
(a1-2-18) 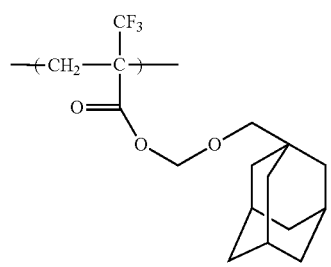
(a1-2-19) 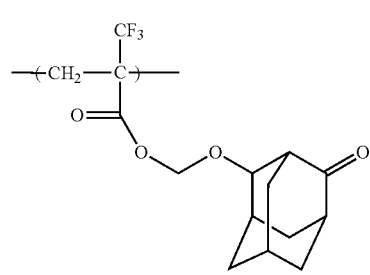
(a1-2-20) 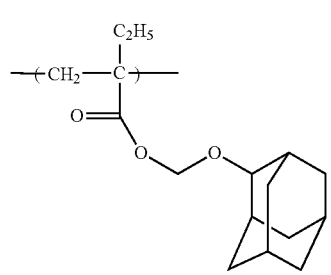
[Chemical Formula 22]
(a1-2-21) 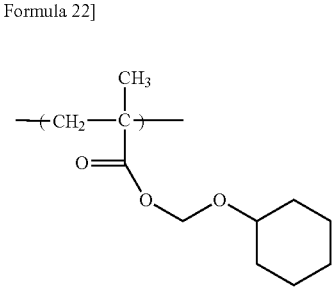
(a1-2-22) 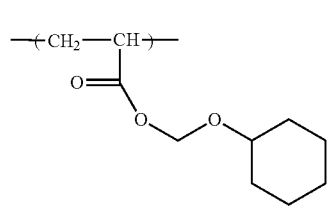
(a1-2-23) 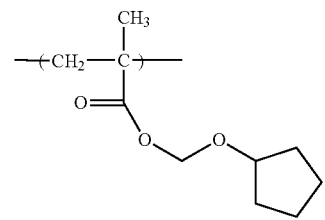

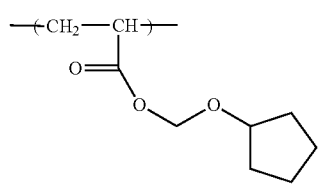
(a1-2-24)
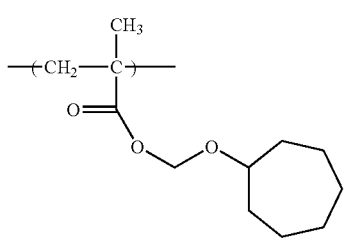
(a1-2-25)
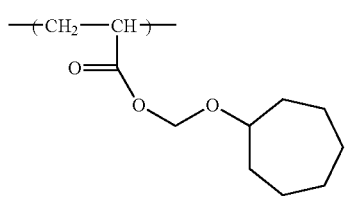
(a-1-2-26)
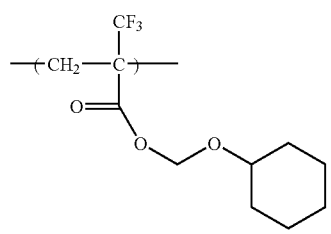
(a1-2-27)
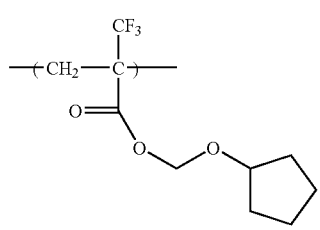
(a1-2-28)
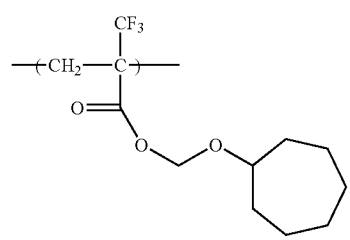
(a1-2-29)
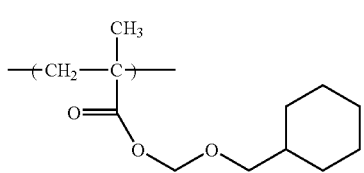
(a1-2-30)
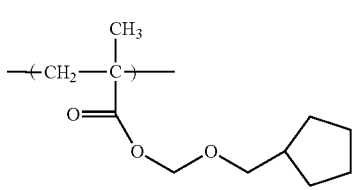
(A1-2-31)
[Chemical Formula 23]
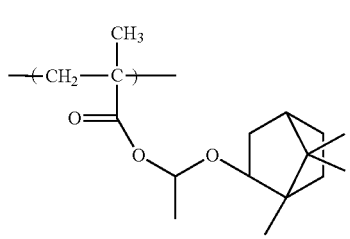
(a1-2-32)
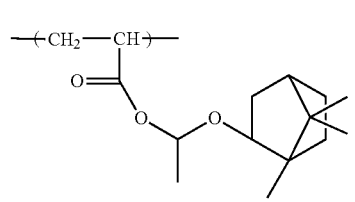
(A1-2-33)
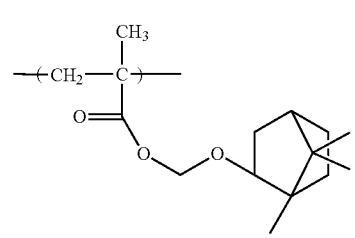
(a1-2-34)
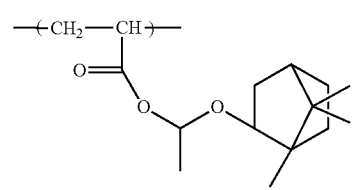
(a1-2-35)
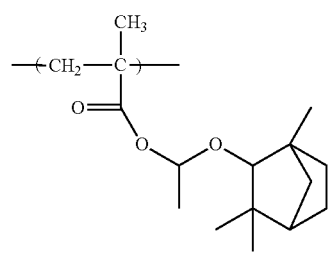
(a1-2-36)
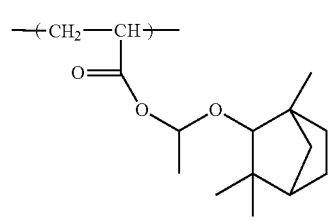
(a1-2-37)

(a1-2-38)
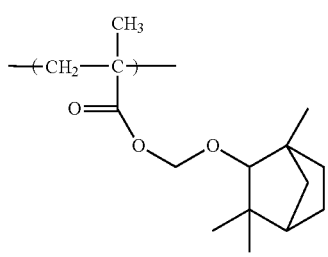
(a1-2-39)
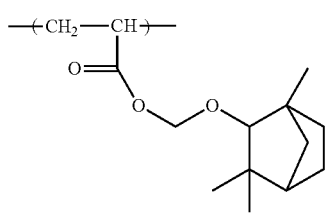
[Chemical Formula 24]
(a1-3-1)
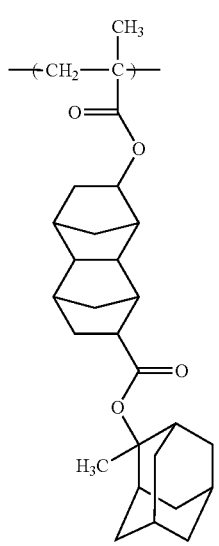
(a1-3-2)
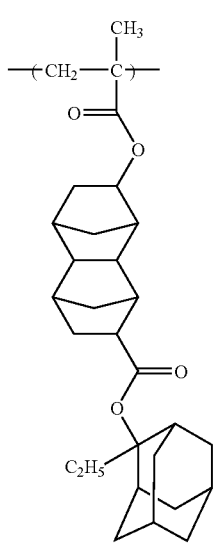
(a1-3-3)
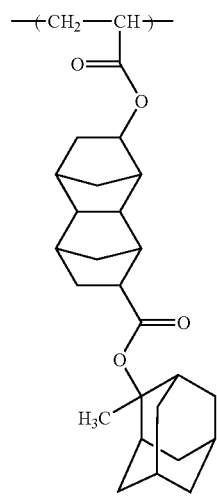
(a1-3-4)
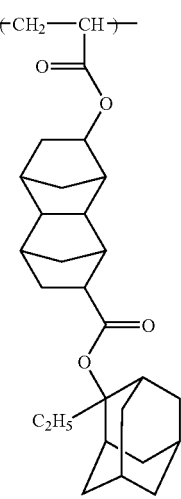
(a1-3-5)
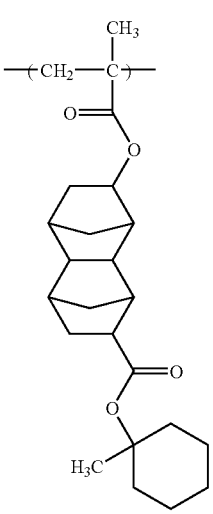

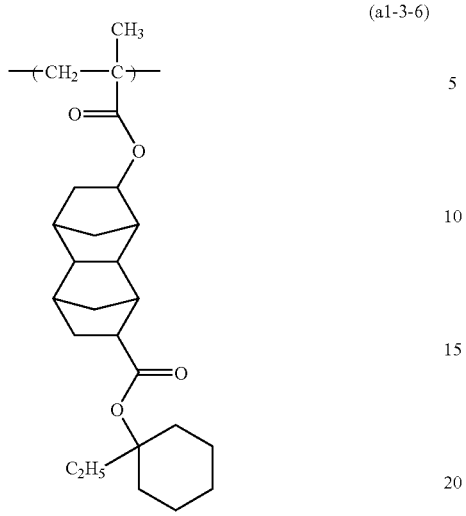
(a1-3-6)
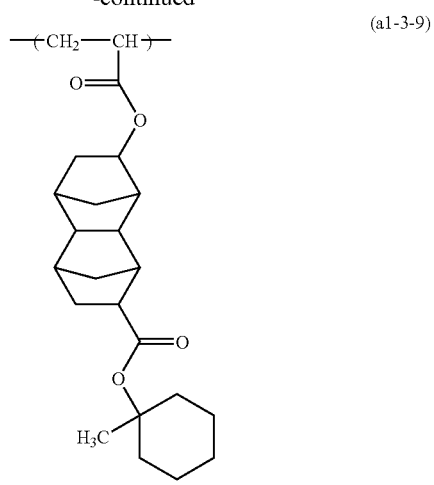
(a1-3-9)
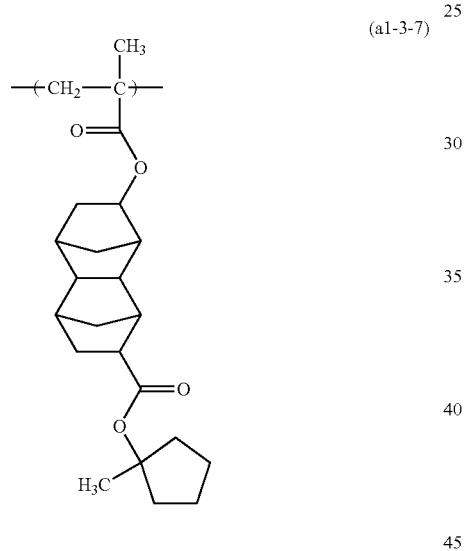
(a1-3-7)
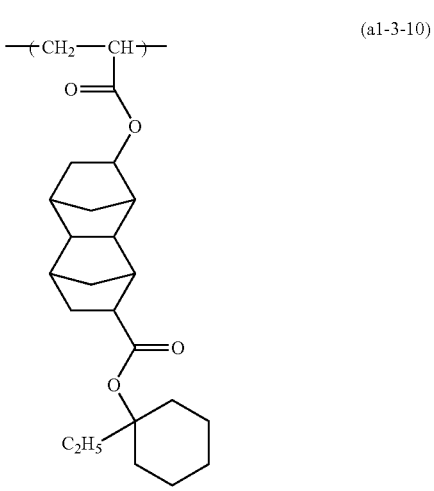
(a1-3-10)
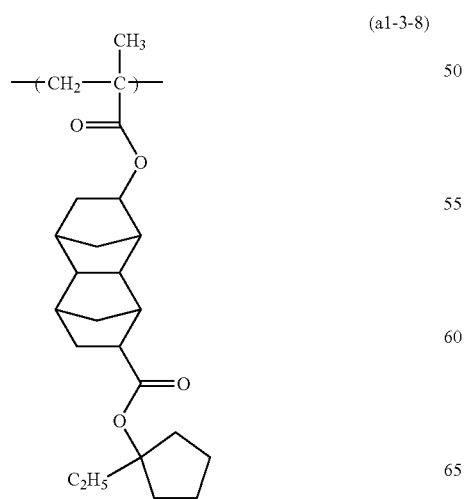
(a1-3-8)
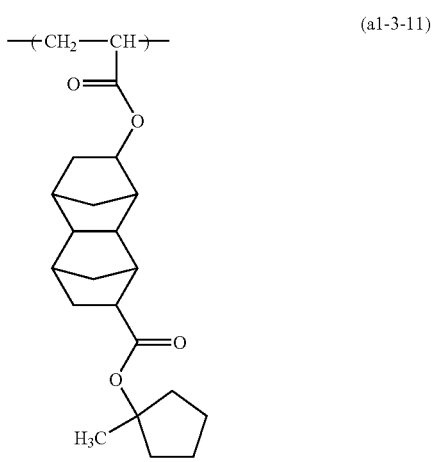
(a1-3-11)

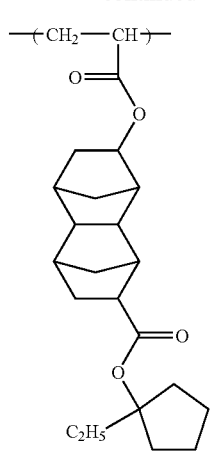
(a1-3-12)
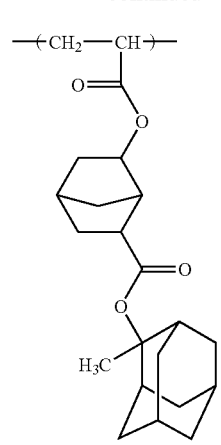
(a1-3-15)
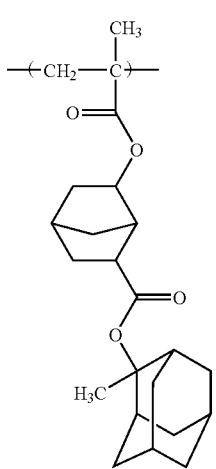
(a1-3-13)
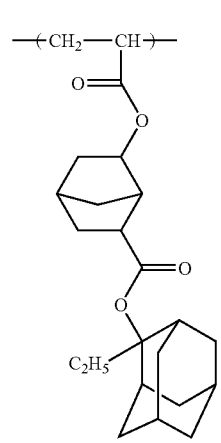
(a1-3-16)
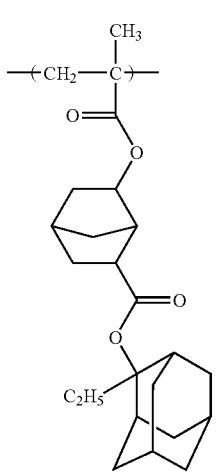
(a1-3-14)
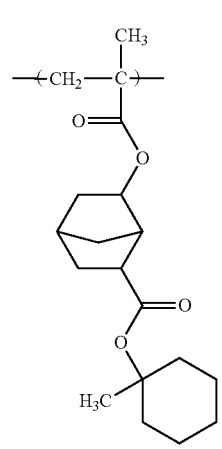
(a1-3-17)

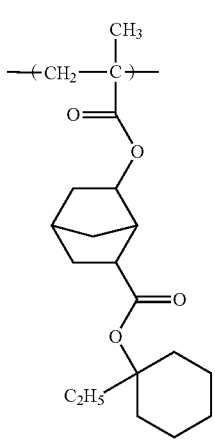 (a1-3-18)
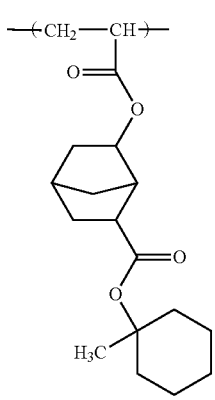 (a1-3-19)
[Chemical Formula 25]
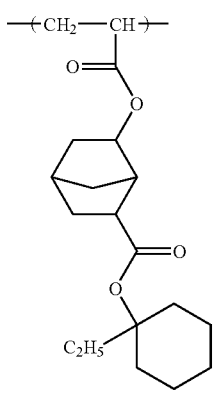 (a1-3-20)
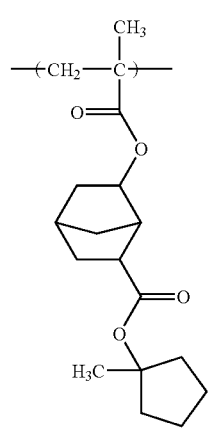 (a1-3-21)
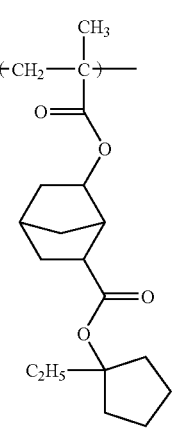 (a1-3-22)
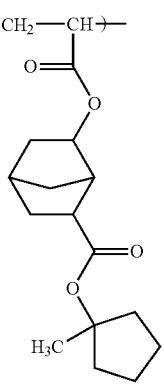 (a1-3-23)
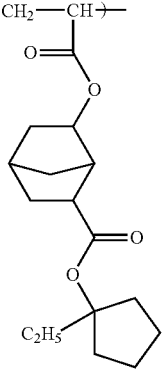 (a1-3-24)
[Chemical Formula 26]
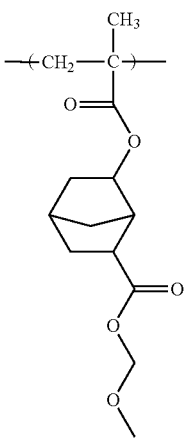 (a1-4-1)

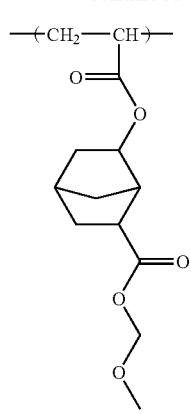 (a1-4-2)
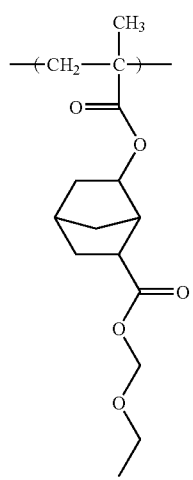 (a1-4-3)
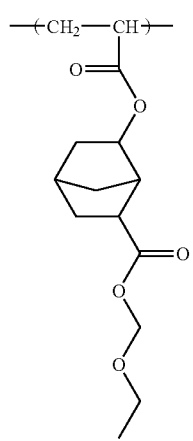 (a1-4-4)
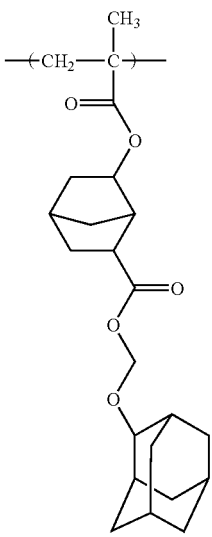 (a1-4-5)
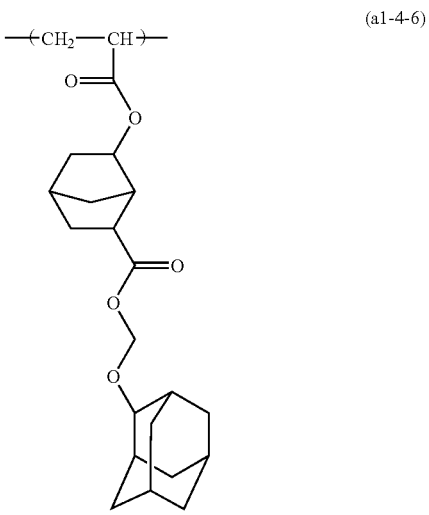 (a1-4-6)
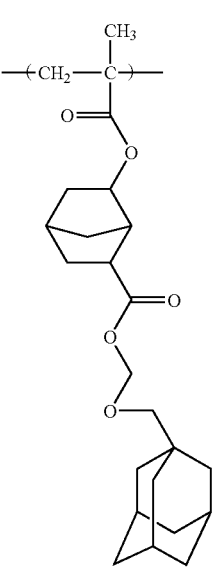 (a1-4-7)

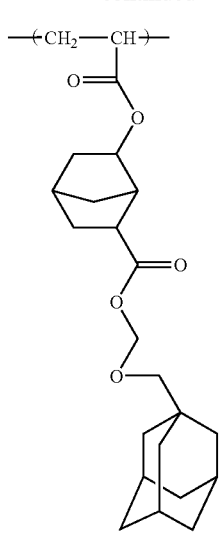
(a1-4-8)
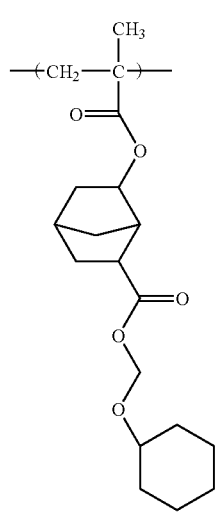
(a1-4-9)
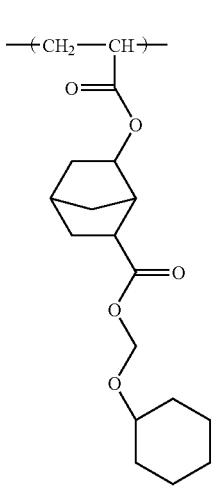
(a1-4-10)
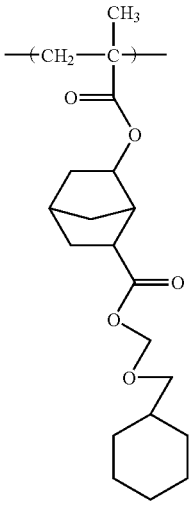
(a1-4-11)
(a1-4-12)
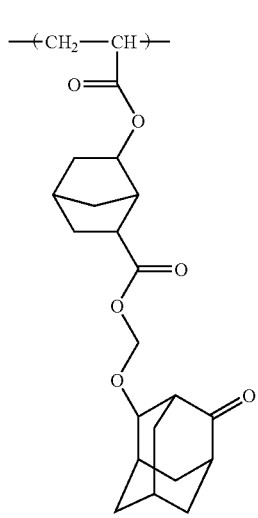
(a1-4-13)

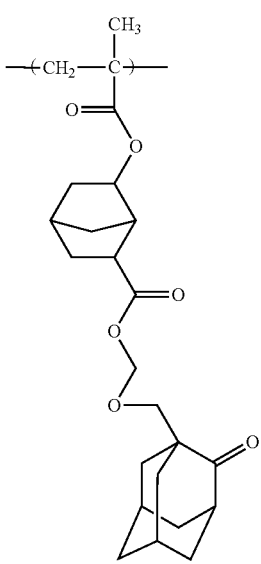 (a1-4-14)
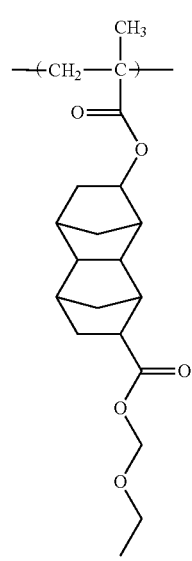 (a1-4-15)
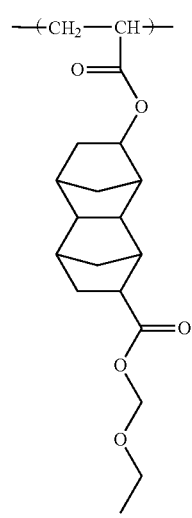 (a1-4-16)
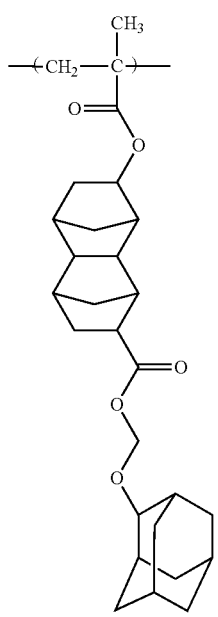 (a1-4-17)
[Chemical Formula 27]
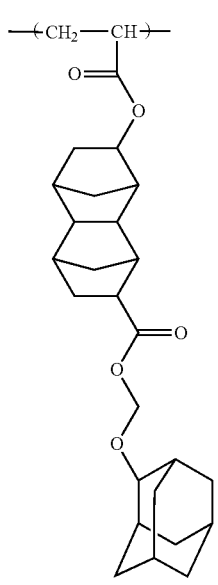 (a1-4-18)

-continued
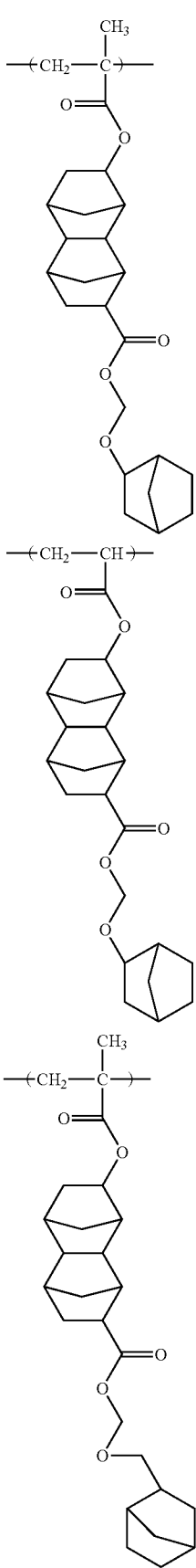
(a1-4-19)
(a1-4-20)
(a1-4-21)
(a1-4-22)
(a1-4-23)

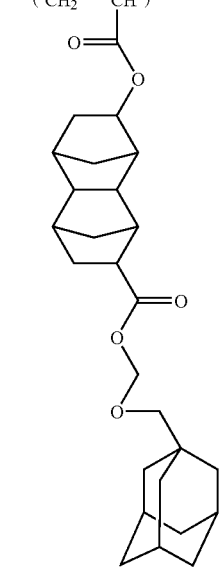
(a1-4-24)
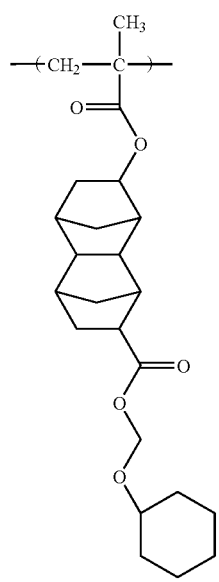
(a1-4-25)
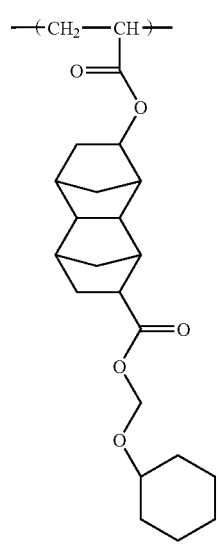
(a1-4-26)
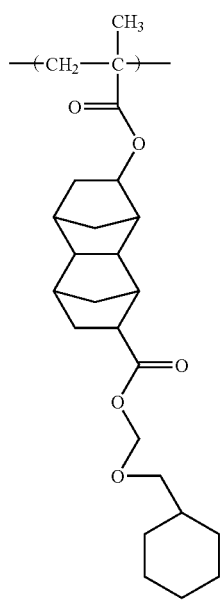
(a1-4-27)
(a1-4-28)

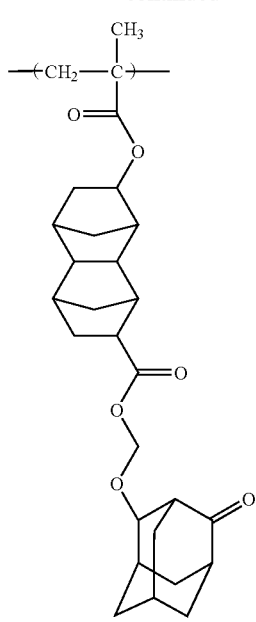 (a1-4-29)
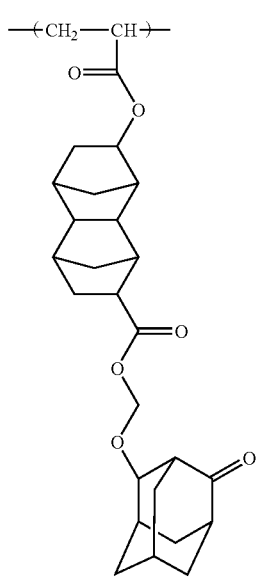 (a1-4-30)
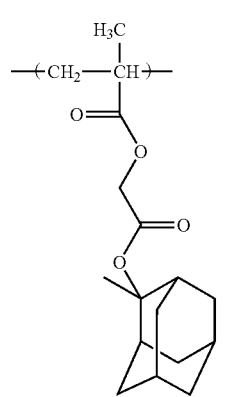 (a1-4-31)
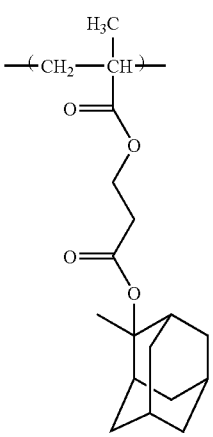 (a1-4-32)
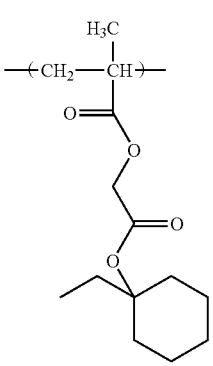 (a1-4-33)
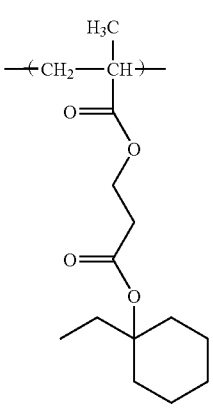 (a1-4-34)
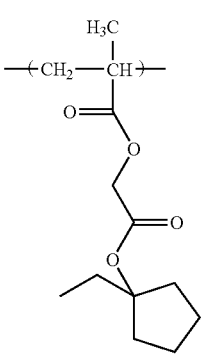 (a1-4-35)

(a1-4-36) 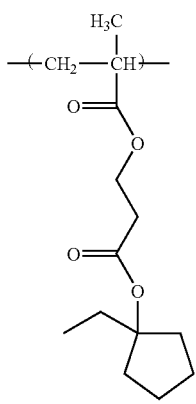

(a1-4-37) 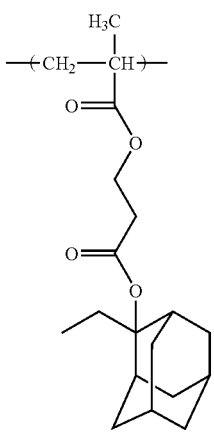

(a1-4-38) 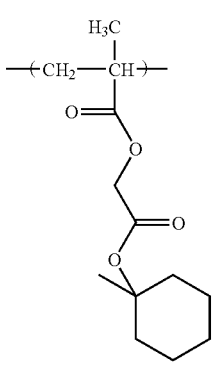

(a1-4-39)

(a1-4-40) 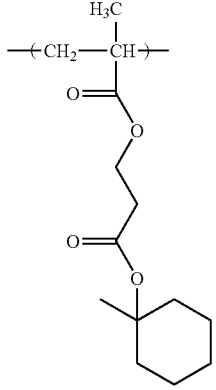

(a1-4-41) 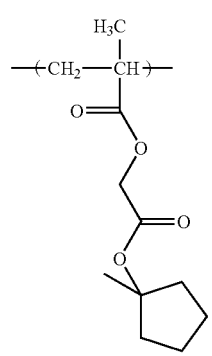

(a1-4-42) 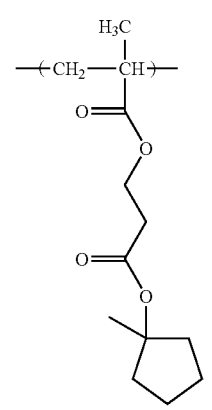

Among these, structural units represented by general formula (a1-1) are preferable. More specifically, at least one structural unit selected from the group consisting of structural units represented by formulas (a1-1-1) to (a-1-1-6) and (a1-1-35) to (a1-1-41) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 28]

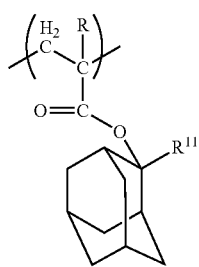
(a1-1-01)

wherein R represents a hydrogen atom, a lower alkyl group or a halogenated lower alkyl group; and $R^{11}$ represents a lower alkyl group.

[Chemical Formula 29]

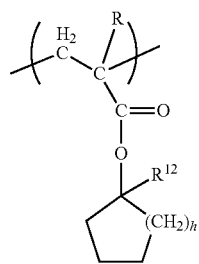
(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

As the structural unit (a1), one type may be used alone, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned rage, a pattern can be easily formed using a resist composition prepared from the component (A1). On the other hand, by making the amount of the structural unit (a1) no more than the upper limit of the above-mentioned range, a good balance can be achieved with the other structural units.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 30]

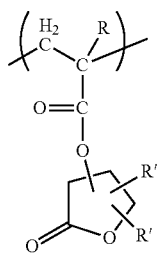
(a2-1)

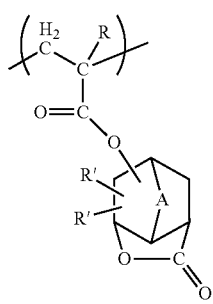
(a2-2)

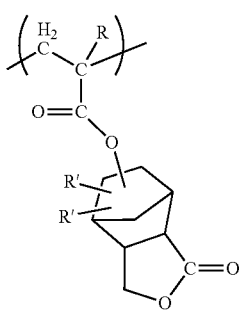
(a2-3)

-continued (a2-4)

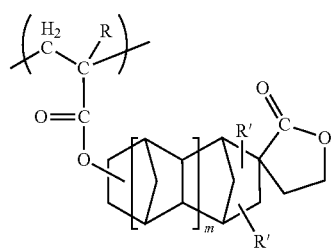

(a2-5)

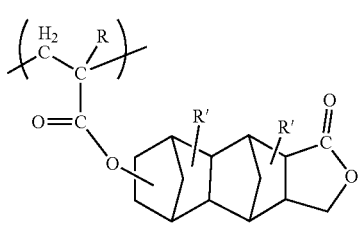

wherein R represents a hydrogen atom, a lower alkyl group or a halogenated lower alkyl group; R' represents a hydrogen atom, a lower alkyl group or an alkoxy group of 1 to 5 carbon atoms; m represents 0 or 1; and A represents an alkylene group of 1 to 5 carbon atoms or an oxygen atom.

In general formulas (a2-1) to (a2-5), R is the same as R in the structural unit (a1).

The lower alkyl group fox R' is the same as the lower alkyl group for R in the structural unit (a1).

Specific examples of alkylene groups of 1 to 5 carbon atoms for A include a methylene group, ethylene group, n-propylene group and isopropylene group.

In the structural units represented by general formulas (a2-1) to (a2-5), in consideration of industrial availability, R' is preferably a hydrogen atom.

Specific examples of structural units represented by general formulas (a2-1) to (a2-5) above are shown below.

[Chemical Formula 31]

(a2-1-1)

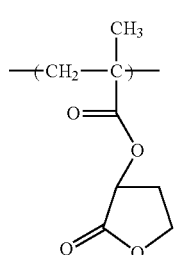

(a2-1-2)

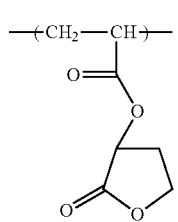

-continued (a2-1-3)

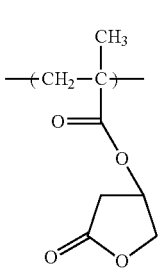

(a2-1-4)

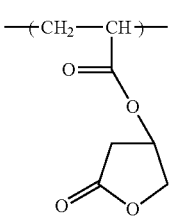

(a2-1-5)

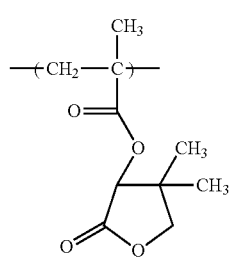

(a2-1-6)

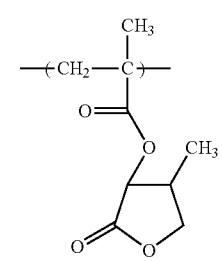

[Chemical Formula 32]

(a2-2-1)

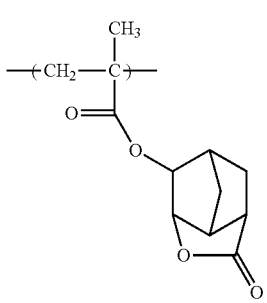

(a2-2-2)

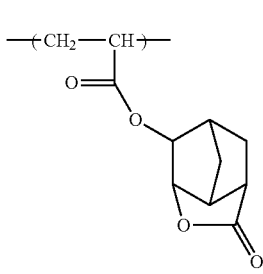

(a2-2-3)
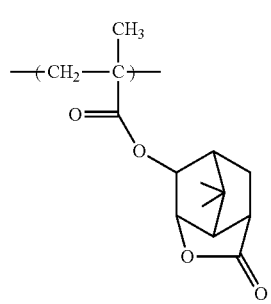
(a2-2-4)
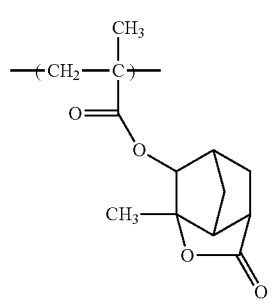
(a2-2-5)
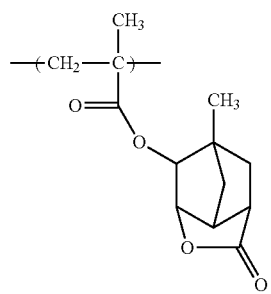
(a2-2-6)
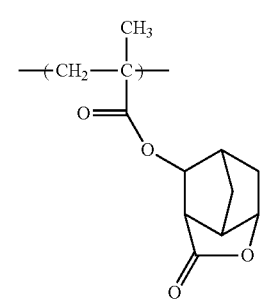
(a2-2-7)
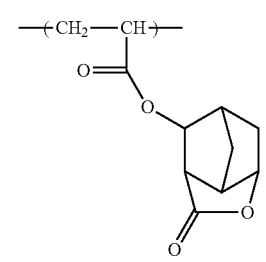
(a2-2-8)
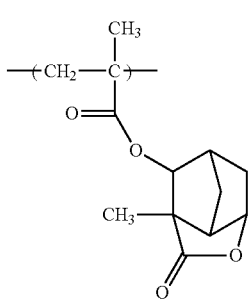
(a2-2-9)
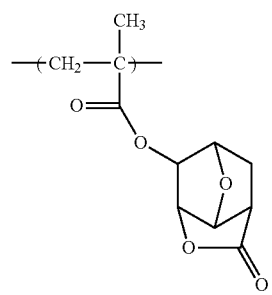
(a2-2-10)
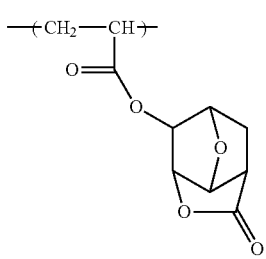
[Chemical Formula 33]
(a2-3-1)
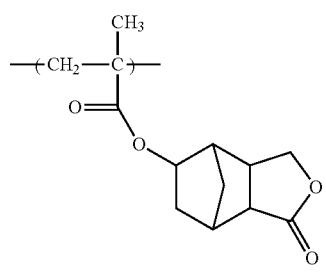
(a2-3-2)
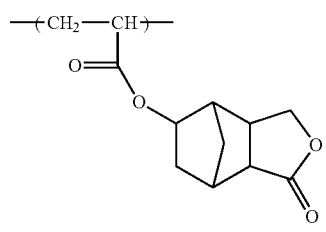
(a2-3-3)
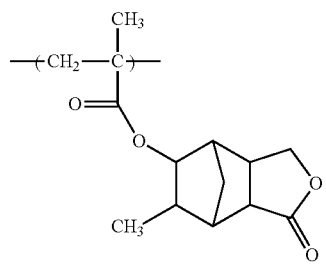

(a2-3-4)
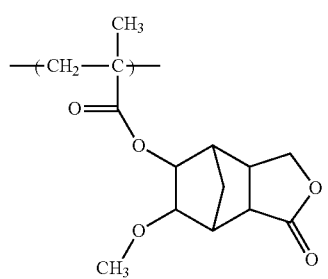
(a2-3-5)
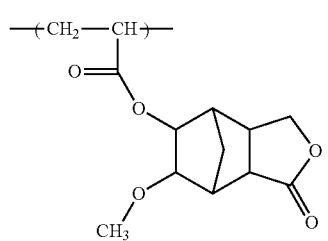
(a2-3-6)
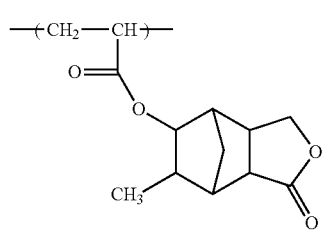
(a2-3-7)
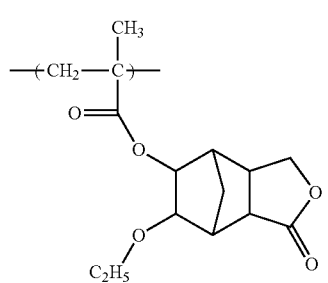
(a2-3-8)
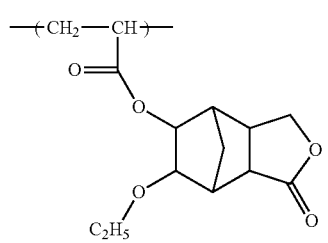
(a2-3-9)
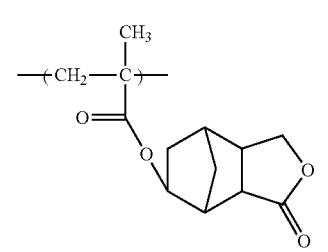
(a2-3-10)
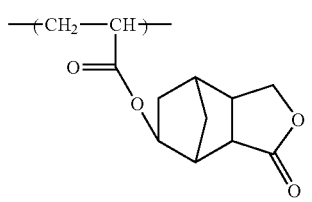
[Chemical Formula 34]
(a2-4-1)
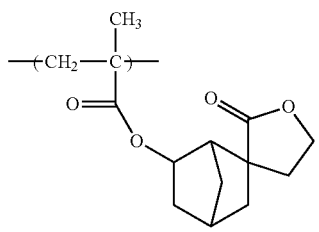
(a2-4-2)
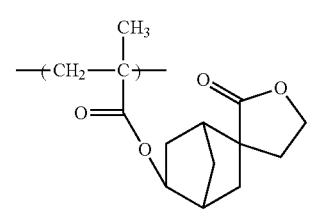
(a2-4-3)
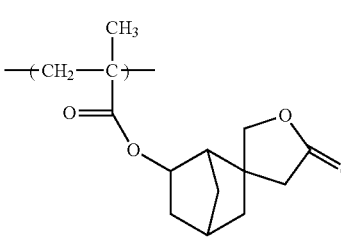
(a2-4-4)
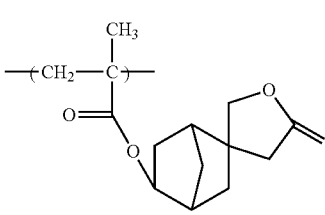
(a2-4-5)
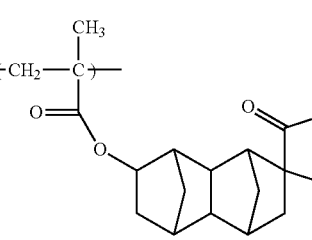
(a2-4-6)
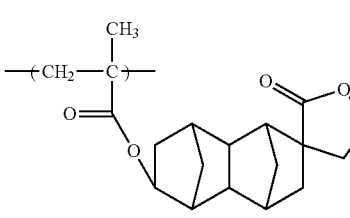

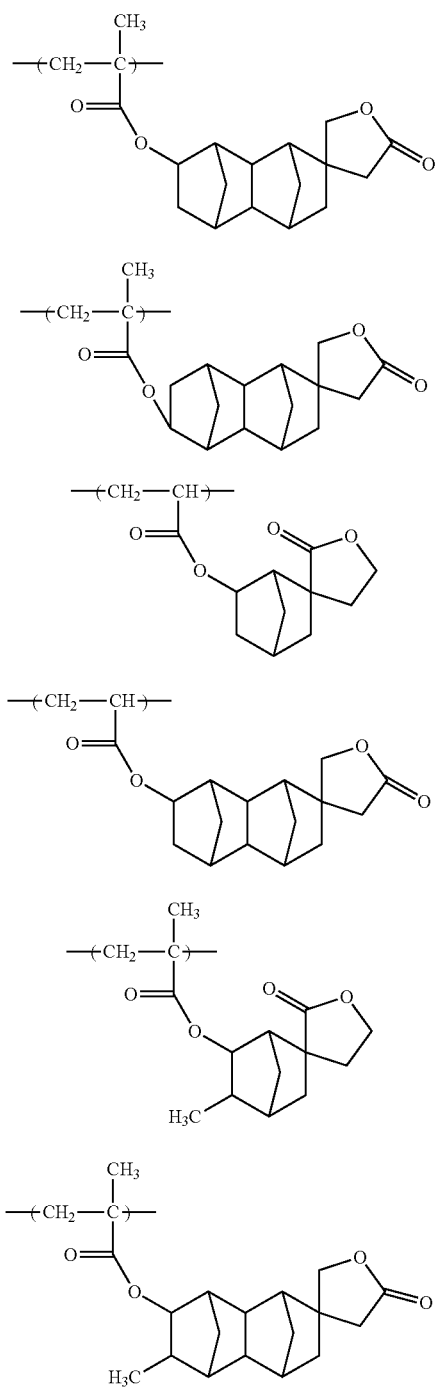
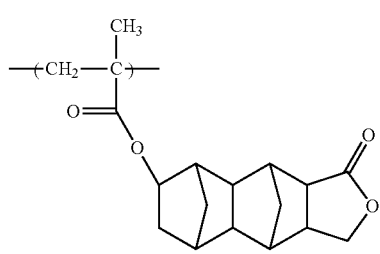
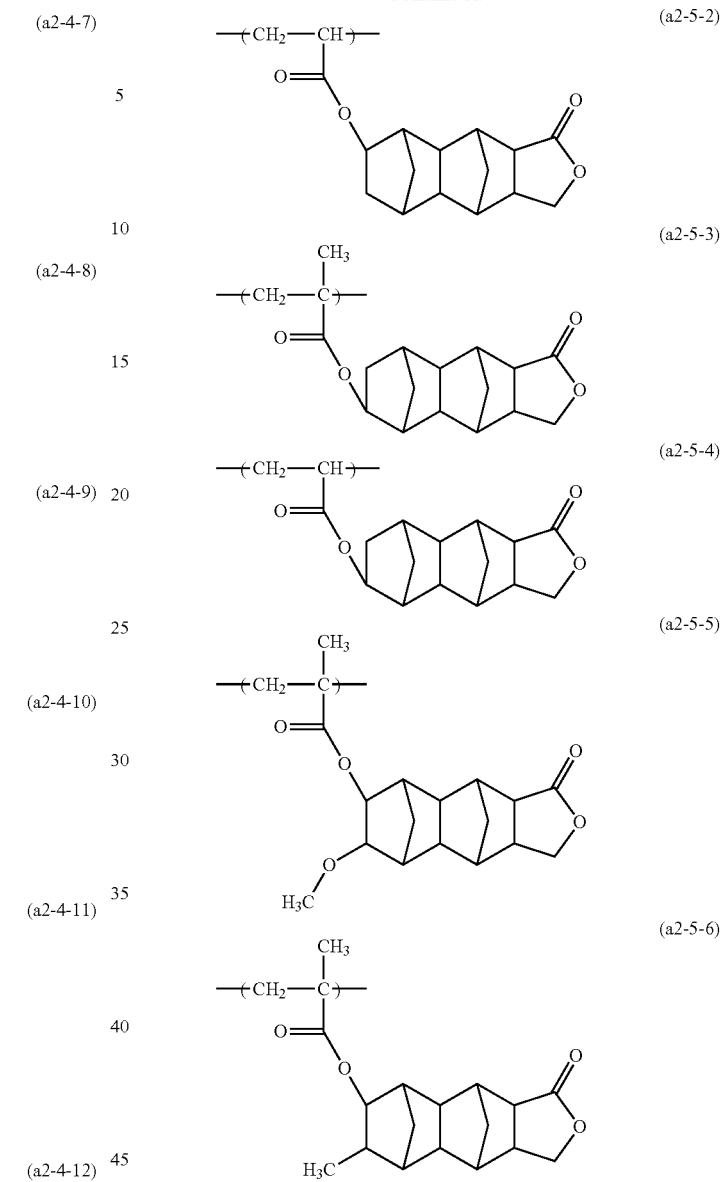

As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-3-1), (a2-3-2), (a2-3-9) and (a2-3-10).

As the structural unit (a2), one type of structural unit may be used, or two or more types may be used in combination.

In the component (A1), the amount of the structural unit (a2) based on the combined total of all structural units consisting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other bad, by making the amount of the structural unit (a2) no more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural it derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 36]

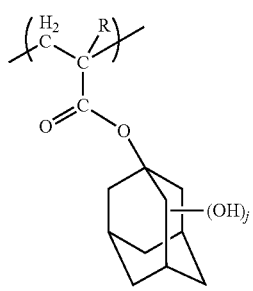

(a3-1)

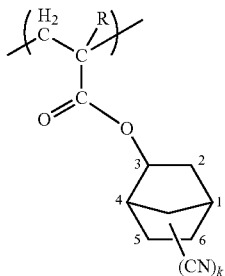

(a3-2)

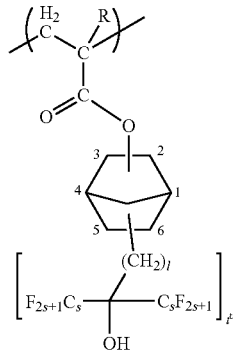

(a3-3)

wherein R is as defined above; j is an integer of 1 to 3; k is an integer of 1 to 3; t' is an integer of 1 to 3; 1 is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1,1 is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structure units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived Thom an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 37]

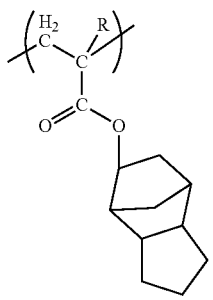

(a4-1)

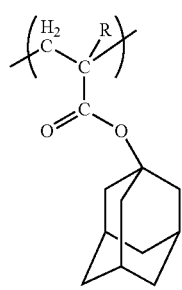

(a4-2)

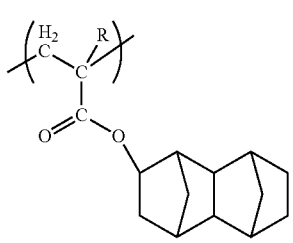

(a4-3)

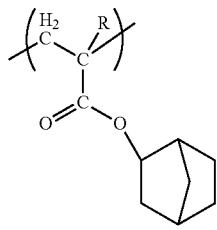

(a4-4)

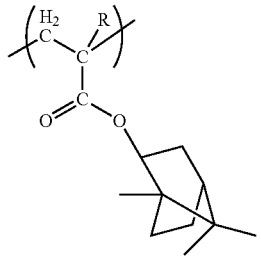

(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) preferably contains a copolymer having the structural units (a1), (a2) and (a3). Examples of such a copolymer include a copolymer consisting of the structural units (a1) and (a2) and (a3), and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferably to use a compound that has a molecular weight of at least 500 and less than 2,000, contains a hydrophilic group, and also contains an acid dissociable, dissolution inhibiting group exemplified above in connection with the component (A1). Specific examples include compounds containing a plurality of phenol skeletons in which apart of the hydrogen atoms within hydroxyl groups have been substituted with the aforementioned acid dissociable, dissolution-inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use it non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl) isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to says the low molecular weight phenol compound is not limited to these examples.

Also, there are no particular limitations on the acid dissociable, dissolution inhibiting group, and suitable examples include the groups described above.

As the component (A), one type may be used, or two or more types may be used in combination.

In the resist composition of the present invention, the amount of the component (A) can be appropriately adjusted depending on the thickness of the resist film to be formed, and the like.

<Component (B)>

As the component (B), there is no particular limitation, and any of the known acid generators used in conventional chemically amplified resist compositions can be used. Examples of these acid generators are numerous, and include onium salt-based acid generators such as iodonium salts and sulfon salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator a compound represented by general formula (b-1) or (b-2) shown below can be preferably used.

[Chemical Formula 38]

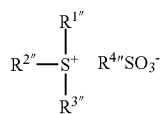

(b-1)

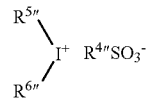

(b-2)

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) way be bonded to each other to form a ring with the sulfur atom; and $R^{4\prime\prime}$ represents an alkyl group, a halogenated alkyl group, an aryl group or an alkenyl group which may have a substituent, with the proviso that at least one of $R^{1\prime\prime}$ to $R^{3\prime\prime}$ represents an aryl group, and at least one of $R^{5\prime\prime}$, and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ in formula (b-1) may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3 to 10-membered ring including the sulfur atom, and it is particularly desirable that the two of $R^{1\prime\prime}$ to $R^{3\prime\prime}$ form a 5 to 7-membered ring including the sulfur atom. When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. As examples of the aryl group, the same as the above-mentioned aryl groups for $R^{1\prime\prime}$ to $R^{3\prime\prime}$ can be exemplified.

R$^{4\prime\prime}$ represents an alkyl group, a halogenated alkyl group, an aryl group or an alkenyl group which may have a substituent.

The alkyl group for R$^{4\prime\prime}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As the halogenated alkyl group for R$^{4\prime\prime}$, a group in which a part or all of the hydrogen atoms of the aforementioned linear, branched or cyclic alkyl group have been substituted with halogen atoms can be exemplified. Examples of the halogen atom include a fluorine atom, a chlorine atom, a bromine atom and an iodine atom, and a fluorine atom is particularly desirable.

In the halogenated alkyl group, the percentage of the number of halogen atoms based on the total number of halogen atoms and hydrogen atoms within the halogenated alkyl group (halogenation ratio (%)) is preferably 10 to 100%, more preferably 50 to 100%, and most preferably 100%. Higher halogenation ratio is preferable because the acid strength increases.

The aryl group for R$^{4\prime\prime}$ is preferably an aryl group of 6 to 20 carbon atoms.

The alkenyl group for R$^{4\prime\prime}$ is preferably an alkenyl group of 2 to 10 carbon atoms.

With respect to R$^{4\prime\prime}$, the expression "may have a substituent" means that a part or all of the hydrogen atoms within the aforementioned linear, branched or cyclic alkyl group, halogenated alkyl group, aryl group or alkenyl group may be substituted with substituents (atoms other than hydrogen atoms, or groups).

R$^{4\prime\prime}$ may have one substitute or two or more substituents.

Examples of the substituent include a halogen atom, a hetero atom, an alkyl group, and a group represented by the formula R$^5$—O— (wherein R$^5$ represents a monovalent aromatic organic group, a monovalent aliphatic hydrocarbon group or a hydroxyalkyl group).

As the halogen atom and the alkyl group, the same as the halogen atom and alkyl group within the halogenated alkyl group for R$^{4\prime\prime}$ may be exemplified.

Examples of the hetero atom include an oxygen atom, a nitrogen atom and a sulfur atom.

With respect to the group represented by the formula R$^5$—O—, examples of the monovalent aromatic organic group for R$^5$ include aryl groups in which one hydrogen atom has been removed from an aromatic hydrocarbon ring, such as a phenyl group, a biphenyl group, a fluorenyl group, a naphthyl group, an anthryl group, and a phenanthryl group; heteroaryl groups in which some of the carbon atoms constituting the ring(s) of these groups are substituted with hetero atoms such as an oxygen atom, a sulfur atom, and a nitrogen atom; and arylalkyl groups such as a benzyl group, a phenethyl group, 1-naphthylmethyl group, a 2-naphthylmethyl group, a 1-naphthylethyl group and a 2-naphthylethyl group.

The alkyl chain within the arylalkyl group preferably has 1 to 4 carbon atom, more preferably 1 or 2, and most preferably 1.

These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated alkyl group is preferably a fluorinated alkyl group. Examples of halogen atoms include a fluorine atom, a chlorine atom, a bromine atom and an iodine atom, and a fluorine atom is preferable.

As the monovalent aromatic organic group for R$^5$, an arylalkyl group is preferable, an arylmethyl group is more preferable, and a naphthylmethyl group is most preferable.

As the monovalent aliphatic hydrocarbon group for R$^5$, for example, a linear, branched or cyclic, monovalent saturated hydrocarbon group of 1 to 15 carbon atoms, or a linear or branched, monovalent unsaturated hydrocarbon group of 2 to 5 carbon atoms can be mentioned.

Examples of linear, monovalent saturated hydrocarbon groups include a methyl group, ethyl group, propyl group, butyl group, pentyl group, hexyl group, heptyl group, octyl group, nonyl group and decanyl group.

Examples of branched, monovalent saturated hydrocarbon groups include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The cyclic, monovalent saturated hydrocarbon group may be either a polycyclic group or a monocyclic group. For example, groups in which one hydrogen atom has been removed from a monocycloalkane or a polycycloalkane such as a bicycloalkane, tricycloalkane or tetracycloalkane can be mentioned. Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of linear, monovalent unsaturated hydrocarbon group include a vinyl group, propenyl group (allyl group) and butynyl group.

Examples of branched, monovalent unsaturated hydrocarbon group include 1-methylpropenyl group and 2-methylpropenyl group.

The monovalent aliphatic hydrocarbon group for R$^5$ preferably has 2 to 4 carbon atoms, and it is particularly desirable that the monovalent aliphatic hydrocarbon group have 3 carbon atoms.

The hydroxyalkyl group for R$^5$ is a linear, branched or cyclic, monovalent saturated hydrocarbon group in which at least one hydrogen atom has been substituted with a hydroxyl group. Linear or branched, monovalent saturated hydrocarbon groups in which one or two hydrogen atoms have been substituted with hydroxyl groups are preferable. Specific examples include a hydroxymethyl group, hydroxyethyl group, 1-hydroxypropyl group, 2-hydroxypropyl group, 3-hydroxypropyl group and 2,3-dihydroxypropyl group.

The monovalent hydroxyalkyl group for R$^5$ preferably has 1 to 10 carbon atoms, more preferably 1 to 8 carbon atoms, still more preferably 1 to 6 carbon atoms, and most preferably 1 to 3 carbon atoms.

In formula (b-2), R$^{5\prime\prime\prime}$ and R$^{6\prime\prime\prime}$ each independently represents an aryl group or alkyl group. At least one of R$^{5\prime\prime\prime}$ and R$^{6\prime\prime\prime}$ represents an aryl group. It is preferable that both of R$^{5\prime\prime\prime}$ and R$^{6\prime\prime\prime}$ represent an aryl group.

As the aryl group for R$^{5\prime\prime\prime}$ and R$^{6\prime\prime\prime}$, the same as the aryl groups for R$^{1\prime\prime\prime}$ to R$^{3\prime\prime\prime}$ can be exemplified.

As the alkyl group for R$^{5\prime\prime\prime}$ and R$^{6\prime\prime\prime}$, the same as the alkyl groups for R$^{1\prime\prime\prime}$ to R$^{3\prime\prime\prime}$ can be exemplified.

It is particularly desirable that both of R$^{5\prime\prime\prime}$ and R$^{6\prime\prime\prime}$ represents a phenyl group.

As R⁴‴ in formula (b-2), the same as those mentioned above for R⁴‴ in formula (b-1) can be exemplified.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonic, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 39]

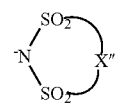
(b-3)

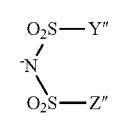
(b-4)

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group of X" or those of the alkyl group of Y" and Z" within the range of the number of carbon atoms, the better the solubility in a resist solvent.

Further, in the alkylene group of X" or the alkyl group of Y" and Z", it is preferable that the number of hydrogen atoms substituted with fluorine atoms is as large as possible, as the acid strength increases, and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (b-5) or (b-6) shown below may be used.

[Chemical Formula 40]

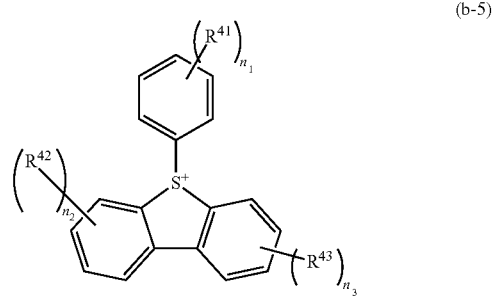
(b-5)

-continued (b-6)

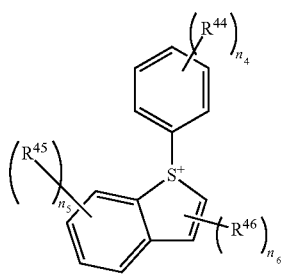

wherein $R^{41}$ to $R^{46}$ each independently represents an alkyl group, an acetyl group, an alkoxy group, a carboxy group, a hydroxyl group or a hydroxyalkyl group; $n_1$ to $n_5$ each independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

When the subscripts $n_1$ to $n_6$ of $R^{41}$ to $R^{46}$ represent an integer of 2 or more, the plurality of $R^{41}$ to $R^{46}$ may be the same or different $n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4''}SO_3^-$) for onium salt-based acid generators represented by general formula (b-1) or (b-2) shown above; ad anion moieties represented by general formula (b-3) or (b-4) shown above.

In the present description, an oximesulfonate-based acid generator is a compound having at least one group represented by general formula (B-1) shown below, and has a feature of generating acid by irradiation. Such oxime-sulfonate-based acid generators are widely used for a chemically amplified resist composition, and can be appropriately selected.

[Chemical Formula 41]

(B-1)

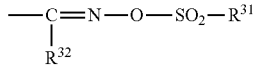

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a suit atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and at iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 42]

(B-2)

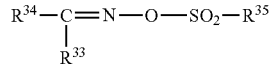

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 43]

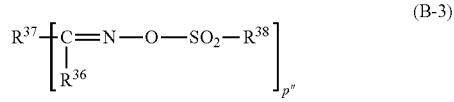

where $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxine sulfonate-based acid generators disclose in WO 2004/074242A2 (Examples 1 to 40 described at pages 65 to 85) may be preferably used.

Among these, as preferable examples, the following can be exemplified.

[Chemical Formula 44]

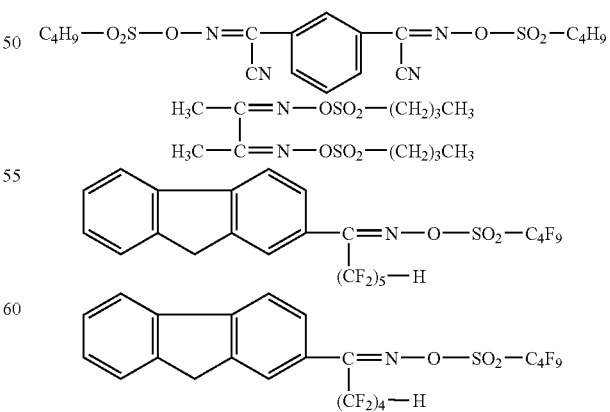

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, an 1,10-bis(cyclohexylsulfonyldiazomethylsulfonyl)decane, may be exemplified.

As the component (B), one type of acid generator may be used, or two or more types may be used in combination.

In the present invention, as the component (B), it is preferable to use an onium salt having a fluorinated alkylsulfonic acid ion, which may have a substituent, as the anion moiety.

In the resist composition for immersion exposure according to the present invention, the amount of the component (B) is preferably 0.5 to 30 parts by weight, and more preferably 1 to 10 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (C)>

The component (C) is the aforementioned fluorine-containing compound (C) of the present invention.

As the component (C), one type may be used, or two or more types may be used in combination.

In the resist composition for immersion exposure according to the present invention, the amount of the component (C) is preferably 0.1 to 20 parts by weight, more preferably 0.5 to 15 parts by weight, still more preferably 0.5 to 10 parts by weight, and most preferably 1 to 5 parts by weight, relative to 100 parts by weight of the component (A). When the amount of the component (C) is at least as large as the lower limit of the above-mentioned range, the hydrophobicity of a resist film formed using the resist composition for immersion exposure is enhanced, and the resist film exhibits favorable hydrophobicity for immersion exposure. On the other hand, when the amount of the component (C) is no more than the upper limit of the above-mentioned range, the lithography properties are improved.

<Optional Component>

In the resist composition for immersion exposure according to the present invention, for improving the resist pattern shape and the post exposure stability of the latent image formed by the pattern-wise exposure of the resist layer, it is preferable to add a nitrogen-containing organic compound (D) (hereafter referred to as the component (D)) as an optional component.

A multitude of these components (D) have already been proposed, and any of these known compounds may be used, although a cyclic amine, an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as triethylamine, trietylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

As the component (D), one type of acid generator may be used, or two or more types may be used in combination.

The component (D) is typically used in an amount within a range from 0.01 to 5.0 part by weight, relative to 100 parts by weight of the component (A).

Furthermore, in the resist composition for immersion exposure according to the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphors oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the abovementioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

If desired, other miscible additives can also be added to the positive resist composition for immersion exposure according to the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent (S)>

The resist composition for immersion exposure according to the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butolactone; ketones such as acetone; methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, a membrane filter or the like.

The resist composition fox immersion exposure according to the present invention exhibits excellent lithography properties and hydrophobicity (hydrophilicity) favorable for immersion exposure, which are properties required for a resist composition for immersion exposure. Therefore, the resist composition of the present invention can be preferably used for immersion exposure.

A resist film formed using the resist composition for immersion exposure according to the present invention contains the component (C) (the fluorine-containing compound (C) of the present invention).

By virtue of containing a fluorine compound, the component (C) exhibits high hydrophobicity. Further, by virtue of containing the group —CO—$R^2$ bonded to Q, the component (C) exhibits increased hydrophilicity under basic conditions. The reason for this is that by action of a base, —CO—$R^2$ is dissociated, and a hydrophilic group (-QH) is generated.

Therefore, a resist film formed using the resist composition for immersion exposure according to the present invention in which the component (C) is blended with the component (A) and the component (B) exhibits high hydrophobicity prior to contacting with an alkali developing solution (e.g., during immersion exposure), and the hydrophilicity thereof is enhanced by contacting with an alkali developing solution.

As described above, a resist film formed using the resist composition for immersion exposure according to the present invention exhibits high hydrophobicity during immersion exposure. Therefore, the resist film exhibits an excellent water tracking ability (tacking ability of water with respect to the movement of the lens) which is required when immersion exposure is conducted using a scanning-type immersion exposure apparatus as disclosed in Non-Patent Document 1.

Further, as hydrophilicity is enhanced during alkali developing, the resist composition for immersion exposure according to the present invention is capable of effectively reducing defects caused by immersion exposure. More specifically, in liquid immersion lithography, when immersion exposure of a resist film is conducted, the solubility of the exposed portions in an alkali developing solution changes. For example, in the case of a positive resist composition, the solubility of the exposed portions in an alkali developing is increased, whereas in the case of a negative resist composition, the solubility of the expose portions in an alkali developing is decreased. By conducting alkali developing, the exposed portions are removed in the case of a positive resist composition, whereas the unexposed portions are removed in the case of a negative resist composition, ad as a result, a resist pattern is formed.

On the surface of the resist film at portions which were not irradiated with radial rays by immersion exposure (e.g., unexposed portions in the case of a positive resist composition), defects (water mark defects, and the like) caused by the influence of the immersion medium such as water are likely to be generated following developing. However, since the hydrophilicity of a resist film formed using the resist composition for immersion exposure according to the present invention is enhanced during developing, generation of such defects can be reduced.

Further, by using the resist composition for immersion exposure according to the present invention, elution of a substance from the resist film during immersion exposure can be suppressed.

As described above, immersion exposure is a method in which exposure (immersion exposure) is conduced in a state where the region between the lens and the resist layer formed on a wafer (which was conventionally filled with air or an inert gas such as nitrogen) is filled with a solvent (a immersion medium) that has a larger refractive index than the refractive index of air. In immersion exposure, when the resist film comes into contact with the immersion medium, elution of substances within the resist film (component (B), component (C), and the like) into the immersion medium occurs. This elution of a substance causes phenomenons such as degeneration of the resist film and change in the refractive index of the immersion medium, thereby adversely affecting the lithography properties.

The amount of the eluted substance is affected by the properties of the resist film surface (e.g., hydrophilicity, hydrophobicity, and the like). Therefore, it is presumed that the amount of eluted substance can be reduced by enhancing the hydrophobicity of the resist film surface.

As the resist composition for immersion exposure according to the present invention includes the component (C) containing a fluorine atom, the resist composition exhibits high hydrophobicity prior to conducting exposure ad developing, as compared to a resist composition containing no component (C). Therefore, it is presumed that the resist composition for immersion exposure according to the present invention can suppress elution of a substance.

As elution of a substance can be suppressed, by using the resist composition for immersion exposure according to the present invention, phenomenons such as degeneration of the resist film and change in the refractive index of the immersion medium, which occur dining immersion exposure, can be suppressed. Further, as variation in the refractive index of the immersion medium can be suppressed, a resist pattern having an excellent shape can be formed. Furthermore, the level of contamination of the lens within the exposure apparatus can be lowered. Therefore, there is no need for protection against these disadvantages, and hence, the present invention can contribute to simplifying the process and the exposure apparatus.

In addition, a resist film formed using the resist composition for immersion exposure according to the present invention hardly swells by water. Therefore, a very fine resist pattern can be formed with a high precision.

Also, the resist composition for immersion exposure according to the present invention exhibits excellent lithography properties with respect to sensitivity, resolution, etching resistance and the like, and is capable of forming a resist pattern without any practical problems when used as a resist for immersion exposure. For example, by using the resist composition for immersion exposure according to the present invention, a very fine resist pattern with a size of no more than 120 nm can be formed.

The hydrophobicity of a resist film can be evaluated by measuring the contact angle thereof against water, for example, the static contact angle (the contact angle between the surface of a water droplet on the resist film in a horizontal step and the resist film surface), the dynamic contact angle (the contact angle at which a water droplet starts to slide when the resist film is inclined (sliding angle), the contact angle at the front-end point of the water droplet in the sliding direction (advancing angle) and the contact angle at the rear-end point of the water droplet in the sliding direction (receding angle)). For example, the higher the hydrophobicity of a resist film, the higher the static angle, advancing angle and receding angle, and smaller the sliding angle.

As shown in FIG. 1, when a droplet 1 is placed on a plane 2 and the plane 2 is gradually inclined the advancing angle is the angle $\theta_1$ formed between the lower end 1a of the droplet 1 and the plane 2 as the droplet 1 starts to move (slide) on the plane 2. Further, at this time (when the droplet 1 starts to move (slide) on the plane 2), the receding angle is the angle $\theta_2$ formed been the upper end 1b of the droplet 1 and the plane 2, and the sliding angle is the inclination angle $\theta_3$ of the plane 2.

In the present description, the advancing angle, receding angle and sliding angle are measured in the following manner.

First, a resist composition solution is spin-coated onto a silicon substrate, and then heated at a temperature of 110° C. for 60 seconds to form a resist film.

Subsequently, the contact angles can be measured using commercially available measurement apparatuses such as DROP MASTER-700 (product name; manufactured by Kyowa Interface Science Co. Ltd.) AUTO SLIDING ANGLE: SA-30 DM (product name; manufactured by Kyowa Interface Science Co. Ltd.), and AUTO DISPENSER: AD-31 (product name; manufactured by Kyowa Interface Science Co. Ltd).

With respect to a resist film formed using the resist composition for immersion exposure according to the present invention, it is preferable that the receding angle as measured prior to conducting immersion exposure and developing be 50 degrees or more, more preferably 50 to 150 degrees, still more preferably 50 to 130 degrees, and most preferably 53 to 100 degrees. When the receding angle is at least as large as the lower limit of the above-mentioned range, the effect of suppressing the elution of a substance dog immersion exposure is enhanced. The reason for this has not been elucidated yet, but it is presumed that one of the main reasons is related to the hydrophobicity of the resist film. More specifically, it is presumed that since an aqueous substance such as water is used as the immersion medium, higher hydrophobicity has an influence on the swift removal of the immersion medium from the surface of the resist film after the immersion exposure. On the other handy when the receding angle is no more than the upper limit of the above-mentioned range, the lithography properties become satisfactory.

For the same reasons as described above, with respect to a resist film formed using the resist composition for immersion exposure according to the present invention, it is preferable that the static contact angle as measured prior to conducting immersion exposure and developing be 60 degrees or more, more preferably 63 to 95 degrees, and most preferably 65 to 95 degrees.

Further, with respect to a resist film formed using the resist composition for immersion exposure according to the present invention, it is preferable that the sliding angle as measured prior to conducting immersion exposure and developing be 36 degrees or lower, more preferably 10 to 36 degrees, still more preferably 7 to 30 degrees, and most preferably 14 to 27 degrees. When the receding angle is no more than the upper limit of the above-mentioned range, the effect of suppressing the elution of a substance during immersion exposure is enhanced. On the other hand, when the sliding angle is at least as large as the lower limit of the above-mentioned range, the lithography properties become satisfactory.

The level of the above-mentioned various angles (dynamic contact angle (advancing angle, receding angle and sliding angle) and static contact angle) can be adjusted by the formulation of the resist composition for immersion exposure, for example, the type and amount of the component (C), and the type of the component (A). For example, by increasing the amount of the component (C), the hydrophobicity of the obtained resist composition can be enhance and the advancing angle, receding angle and static contact angle becomes large, whereas the sliding angle becomes small.

As described above, the resist composition for immersion exposure according to the present invention exhibits various properties required for a resist material for use in immersion exposure. Therefore, the resist composition of the present invention can be preferably used for immersion exposure.

<<Method of Forming a Resist Pattern>>

The method of forming a resist pattern according to the present invention includes: applying a resist composition for immersion exposure according to the present invention to a substrate to form a resist film on the substrate; subjecting the resist film to immersion exposure; and alkali developing the resist film to form a resist pattern.

A preferable example of the method for forming a resist pattern according to the second aspect of the present invention will be described below.

Firstly, a resist composition for immersion exposure according to the present invention is applied onto a substrate using a spinner or the like; and a prebake (post applied bake (PAB)) is conducted to form a resist film.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) and an organic film such as a lower-layer organic film used in a multilayer resist method can be exemplified.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of for a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film.

After formation of a resist film, an organic antireflection film may be provided on the resist film, thereby forming a triple layer laminate consist of the substrate, the resist film and the antireflection film. The anti-reflection film provided on top of the resist film is preferably soluble in an alkali developing solution.

The steps up until this point can be conducted by using conventional techniques. The operating conditions and the like are appropriately selected depending on the formulation and the characteristics of the resist composition for immersion exposure being used.

Subsequently, the obtained resist film is subjected to selective immersion exposure (liquid immersion lithography) through a desired mask pattern. At this time, the region between the resist film and the lens at the lowermost point of the exposure apparatus is pre-filled with a solvent (immersion medium) that has a larger refractive index than the refractive index of air, and the exposure (immersion exposure) is conducted in this state.

There are no particular limitations on the wavelength used for the exposure, and an ArF excimer laser, KrF excimer laser or $F_2$ excimer laser or the like can be used. The resist composition according to the present invention is effective for KrF or ArF excimer lasers, and is particularly effective for ArF excimer lasers.

The immersion medium preferably exhibits a refractive index larger than the refractive index of air but smaller than the refractive index of the resist film formed from the resist composition for immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

A resist composition for immersion exposure according to the present invention is particularly resistant to my adverse effects caused by water, and because the resulting lithography properties such as sensitivity and shape of the resist pattern are excellent, water is preferably used as the immersion medium which exhibits a refractive index that is larger than the refractive index of air. Furthermore, water is also preferred in terms of cost, safety, environmental friendliness, and versatility.

Subsequently, following completion of the immersion exposure step, post exposure baking (PEB) is conducted, followed by a developing treatment using an alkali developing solution containing an alkali aqueous solution. Thereafter, water rinse is preferably conducted with pure water. This water rinse can be conducted by dripping or spraying water onto the surface of the substrate while rotating the substrate, and washes away the developing solution and those portions of the resist composition for immersion exposure that have been dissolved by the developing solution. Further, by drying, a resist pattern is obtained in which the resist film (coating of the resist composition for immersion exposure) has been patterned into a shape corresponding to the mask pattern.

EXAMPLES

As follows is a description of examples of the present invention, although the scope of the present invention is by no way limited by these examples.

Example 1

6 ml of a THF solution of 3.8 g (31.2 mmol) of pivaloyl chloride was dropwise added to 15 ml of a THF solution having dissolved therein 5 g (26 mmol) of 2,3,5,6-tetrafluoro-4-hydroxystyrene and 5.3 g (52 mmol) of triethylamine, in a nitrogen atmosphere at 0° C. Then, the temperature of the reaction liquid was elevated to room temperature, and the reaction liquid was stirred for 1 hour. After conducting thin-layer chromatography to confirm disappearance of the raw materials, the reaction liquid was cooled to 0° C., and water was added to the reaction liquid to terminate the reaction. Thereafter, water and ethyl acetate were added to the reaction liquid, and extraction was conducted 3 times. Then, the resulting organic phase was washed once with a saturated aqueous solution of ammonium chloride, once with water, and once with saturated salt water, and anhydrous sodium sulfate was added thereto and dried. Then, the solvent was distilled off under reduced pressure, and the resulting product was subjected to recrystallization with heptane/ethyl acetate, thereby obtaining 5.9 g of 2,3,5,6-tetrafluoro-4-trimethylaectoxystyrene (hereafter, referred to as "compound (1)") in the form of a white powder (yield: 82%).

[Chemical Formula 45]

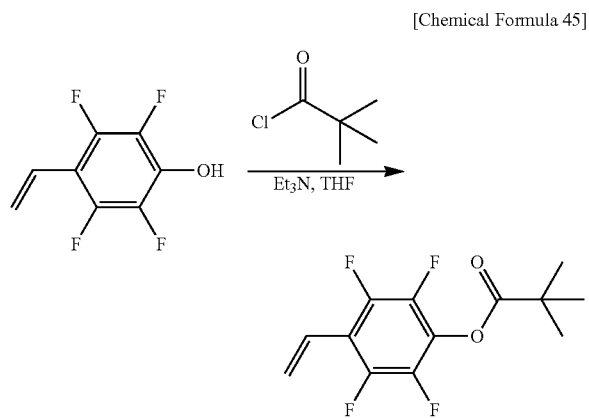

The obtained compound (1) was analyzed by $^1$H-NMR. The results are shown below.

$^1$H-NMR (solvent: CDCl$_3$ 400 MHz), δ(ppm)=6.6 (dd, 1H (H$^b$)), 6.1 (d, 1H (H$^a$)), 5.7 (d, 1H (H$^a$)), 1.4 (s, 9H (H$^c$)).

From the results shown above, it was confirmed that the compound (1) had a structure shown below.

[Chemical Formula 46]

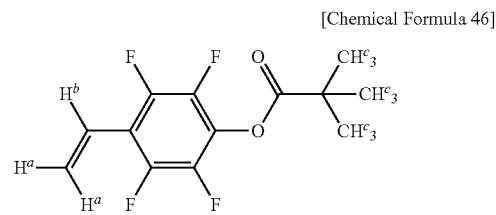

With respect to the obtained compound (1), the following evaluation was performed.

[Reaction Under Basic Condition]

To 20 mg of the compound (1) was added a mixture of THF and a 2.38% by weight aqueous solution of tetramethylammonium hydroxide with a mixing ratio (weight ratio) of 1/1, and the resultant was shaken for 10 seconds. Then, the organic phase and 2,3,5,6-tetrafluoro-4-hydroxystyrene (which was presumed to be a deprotection product) were taken out and subjected to TLC spreading (heptane/ethyl acetate=8/2).

As a result, it was confirmed that a part of the compound (1) had undergone deprotection (dissociation of pivaloyl groups (—CO—C(CH$_3$)$_3$)), and a deprotection product (2,3,5,6-tetrafluoro-4-hydroxystyrene) was generated. (The Rf values of the deprotection product and 2,3,5,6-tetrafluoro-4-hydroxystyrene were the same. Rf value of compound (1): 0.77, Rf value of deprotection product 0.42.)

Example 2

1.00 g (3.62 mmol) of the compound (1) synthesized in Example 1 was dissolved in 1.00 g of toluene, and 0.54 mmol of a polymerization initiator (product name: V-601, manufactured by Wako Pure Chemical Industries, Ltd.) was added thereto and dissolved. The resulting solution was subjected to a polymerization reaction in a nitrogen atmosphere at 80° C. for 2 hours. After the completion of the reaction, the reaction liquid was cooled to room temperature. Then, the reaction liquid was dropwise added to an excess amount of a methanol solution, and an operation to deposit a polymer was performed twice.

The deposited polymer was dried under reduced pressure at room temperature, thereby obtaining 0.6 g of a white powder (yield: 60%). This white powder was designated as "fluorine-containing compound (C)-1".

With respect to (C)-1 the weight average molecular weight and the dispersity were determined by the polystyrene equivalent value as measured by gel permeation chromatography (GPC). As a result, it was found that the weight average molecular weight was 9,900, and the dispersity was 2.29.

[Chemical Formula 47]

(C)-1

Comparative Synthesis Example 1

7.9 g of 7,7,7-trifluoro-3-ethyl-3-heptanol, 0.2 g of 4-dimethylaminopyridine, 7.1 g of triethylamine and 10 g of acetonitrile were charged into a four-necked flask equipped with a stirrer, a thermometer and a funnel, and stirred and dissolved. Then, 6.7 g of methacrylic acid chloride was dropwise added to the resulting solution at about 75° C. over 30 minutes, and the resultant was stirred at the same temperature for 2 hours. Thereafter, the reaction liquid was cooled to room temperature, and washed once with a mixture of 8.8 g of potassium carbonate and 100 ml of water, and once with a 10% salt water. Then, the reaction liquid was dried with anhydrous magnesium sulfate, and concentrated under reduced pressure.

The resulting concentration product was purified by silica gel column chromatography, thereby obtaining 5.7 g of 7,7,7-trifluoro-3-ethyl-3-hepthyl methacrylate.

The $^1$H-NMR data of the obtained 7,7,7-trifluoro-3-ethyl-3-hepthyl methacrylate were as follows.

$^1$H-NMR(CDCl$_3$) δ: 0.82-0.87 (tr, 6H, —CH$_3$), 1.46-1.58 (m, 2H, —CH$_2$—), 1.78-1.97 (m, 9H, =C—CH$_3$, —C—CH$_2$—), 1.98-2.16 (m, 2H, CF$_3$CH$_2$—), 5.49 (s, 1H, C=CH$_2$), 6.01 (s, 1H, C=CH$_2$).

From the results shown above, it was confirmed that the compound had a structure shown below.

[Chemical Formula 48]

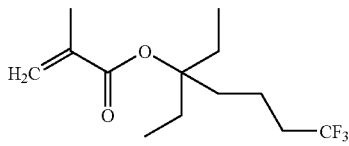

Subsequently, 27 g of tetrahydrofuran and 11.98 g of the 7,7,7-trifluoro-3-ethyl-3-hepthyl methacrylate obtained above were charged into a four-necked flask equipped with a nitrogen-introduction tube, a reflux condenser, a funnel and a thermometer. Then, the four-necked flask was purged with nitrogen, and the temperature was elevated to 67° C. While maintaining the temperature at 67° C., a solution obtained by dissolving 0.30 g of 2,2'-azobis(2,4-dimethylvaleronitrile) in 3 g of tetrahydrofuran was dropwise added to the four-necked flask over 10 minutes. Thereafter, while maintaining the temperature at 67° C., the resultant was stirred for 6 hours, and then cooled to room temperature. The resulting polymerization reaction liquid was dropwise added to an excess amount of a methanol/water mixture, and the precipitated resin was separated by filtration, washed and dried, thereby obtaining 4.0 g of a fluorine-containing compound represented by chemical formula (C)-2 shown below, in the form of a white solid. The weight average molecular weight (Mw) and dispersity (Mw/Mn) in terms of the polystyrene equivalent value were 6,500 and 1.4, respectively.

[Chemical Formula 49]

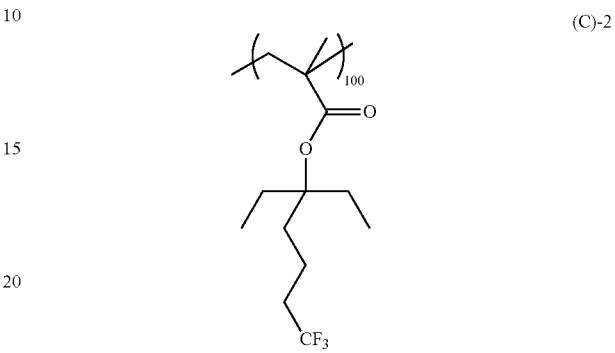

(C)-2

Example 3

8 g (42 mmol) of 2,3,5,6-tetrafluoro-4-hydroxystyrene was added to 40 ml of a THF solution of 8 g (62 mmol) of 3,3,3-trifluoropropionic acid, 14 g (75 mmol) of ethyldiisopropylaminocarbodiimide hydrochloride (EDCl) and 0.5 g (4 mmol) of dimethylaminopyridine (DMAP), in a nitrogen atmosphere at 0° C. Then, the temperature of the reaction liquid was elevated to room temperature, and the reaction liquid was stirred for 3 hours. After conducting thin-layer chromatography to confirm disappearance of the raw materials, the reaction liquid was cooled to 0° C., and water was added to the reaction liquid to terminate the reaction. Thereafter, ethyl acetate was added to the reaction liquid, and extraction was conducted 3 times. Then, the resulting organic phase was washed with water twice. Then, the solvent was distilled off under reduced pressure, and the resulting product was purified by silica get chromatography (purification with heptane/ethyl acetate), thereby obtaining 9 g of a compound (3) represented by formula (3) shown below, in the form of a colorless oily substance (yield: 72%).

[Chemical Formula 50]

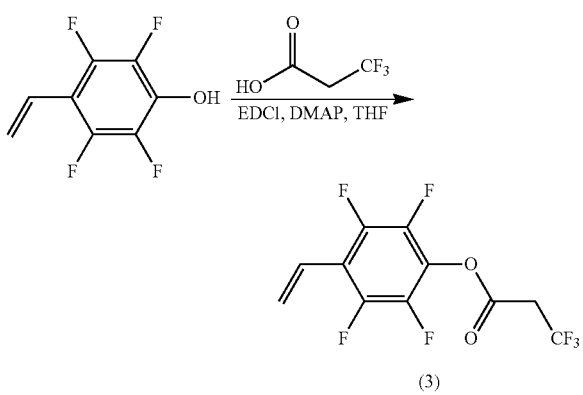

The obtained compound (3) was analyzed by $^1$H-NMR. The results are shown below.

$^1$H-NMR (solvent: CDCl$_3$, 400 MHz): δ(ppm)=6.6 (dd, 1H (H$^b$)), 6.1 (d, 1H (H$^a$)), 5.7 (d, 1H (H$^a$)), 3.5 (m, 2H (H$^c$)).

From the results shown above, it was confirmed that the compound (3) had a structure shown below.

[Chemical Formula 51]

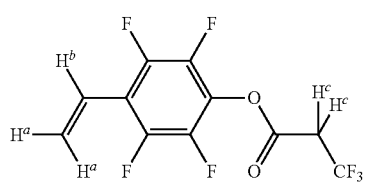

Example 4

2.50 g (8.28 mmol) of the compound (3) synthesized in Example 3 was dissolved in 5.83 g of toluene, and 0.41 mmol of a polymerization initiator (product name: V-601, manufactured by Wako Pure Chemical Industries, Ltd.) was added thereto and dissolved. The resulting solution was subjected to a polymerization reaction in a nitrogen atmosphere at 90° C. for 3 hours. After the completion of the reaction, the reaction liquid was cooled to room temperature. Then, the reaction liquid was dropwise added to an excess amount of a methanol solution, and an operation to deposit a polymer was performed twice.

The deposited polymer was dried under reduced pressure at room temperature, thereby obtaining 1.45 g of a white powder (yield: 58%). This white powder was designated as "fluorine-containing compound (C)-3".

With respect to (C)-3, the weight average molecular weight and the dispersity were determined by the polystyrene equivalent value as measured by gel permeation chromatography (GPC). As a result it was found that the weight average molecular weight was 13,300, and the dispersity was 1.67.

[Chemical Formula 52]

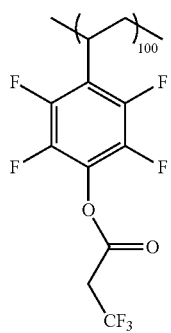

(C)-3

Example 5

3 g (equivalent to 25 mmol) of polyhydroxystyrene (product name: VP8000, manufactured by Nippon Soda Co., Ltd.) was added to 60 ml of a THF solution of 4 g (30 mmol) of 3,3,3-trifluoropropionic acid, 6.2 g (33 mmol) of ethyldiisopropylaminocarbodiimide hydrochloride (EDCl) and 0.5 g (4 mmol) of dimethylaminopyridine (DMAP), in a nitrogen atmosphere at 0° C. Then, the temperature of the reaction liquid was elevated to room temperature, and the reaction liquid was stirred for 3 hours. Thereafter, the reaction liquid was cooled to 0° C., and water was added to the reaction liquid to terminate the reaction. Then, the resulting organic phase was washed with water three times, and the solvent was distilled off under reduced pressure. A THF solution of the resulting product was dropwise added to heptane to perform re-precipitation, thereby obtaining 4.3 g of a fluorine-containing compound (C)-4 represented by formula (4) shown below, in the form of a white solid (yield: 75%).

The obtained fluorine-on compound (C)-4 was analyzed by $^{13}$C-NMR. As a result it was confirmed that —C(=O)—CH$_2$—CF$_3$ was introduced into 74.1 mol % of the hydroxyl groups within the hydroxystyrene as the raw material (introduction ratio; 74.1%). Therefore, in formula (4) shown below, the m:n ratio was 74.1:25.9 (molar ratio).

Further, with respect to (C)-4, the weight average molecular weight and the dispersity were determined by the polystyrene equivalent value as measured by gel permeation chromatography (GPC). As a result, it was found that the weight average molecular weight was 14,000, and the dispersity was 1.08.

[Chemical Formula 53]

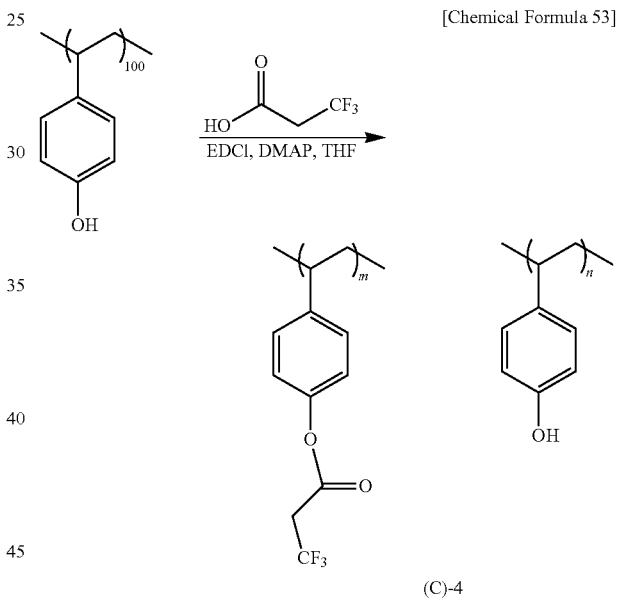

(C)-4

Examples 6 to 9 and Comparative Examples 1 and 2

The components shown in Table 1 were mixed together and dissolved to obtain resist compositions.

TABLE 1

|  | Component (A) | Component (B) | Component (C) | Component (D) | Component (S) |
|---|---|---|---|---|---|
| Ex. 6 | (A)-1 [100] | (B)-1 [8.0] | (C)-1 [1.0] | (D)-1 [1.2] | (S)-1 [1500] |
| Ex. 7 | (A)-1 [100] | (B)-1 [8.0] | (C)-1 [5.0] | (D)-1 [1.2] | (S)-1 [1500] |
| Comp. Ex. 1 | (A)-1 [100] | (B)-1 [8.0] | (C)-2 [1.0] | (D)-1 [1.2] | (S)-1 [1500] |
| Comp. Ex. 2 | (A)-1 [100] | (B)-1 [8.0] | — | (D)-1 [1.2] | (S)-1 [1500] |
| Ex. 8 | (A)-1 [100] | (B)-1 [8.0] | (C)-3 [1.0] | (D)-1 [1.2] | (S)-1 [1500] |

TABLE 1-continued

|  | Component (A) | Component (B) | Component (C) | Component (D) | Component (S) |
|---|---|---|---|---|---|
| Ex. 9 | (A)-1 [100] | (B)-1 [8.0] | (C)-4 [1.0] | (D)-1 [1.2] | (S)-1 [1500] |

In Table 1, the reference characters indicate the following.

(A)-1: a copolymer represented by chemical formula (A)-1 shown below. In the formula, each of the subscript numerals at the lower right of the brackets indicate the ratio (mol %) of the respective structural units.

(B)-1: (4-methylphenyl)diphenylsulfonium nonafluoro-n-butanesulfonate (C)-1: fluorine-containing compound (C)-1 synthesized in Example 2

(C)-2: fluorine-containing compound (C)-2 synthesized in Comparative Synthesis Example 1

(C)-3: fluorine-containing compound (C)-3 synthesized in Example 4

(C)-4: fluorine-containing compound (C)-4 synthesized in Example 5

(D)-1: tri-n-pentylamine (S)-1: a mixed solvent of PGMEA/PGME=6/4 (weight ratio)

[Chemical Formula 54]

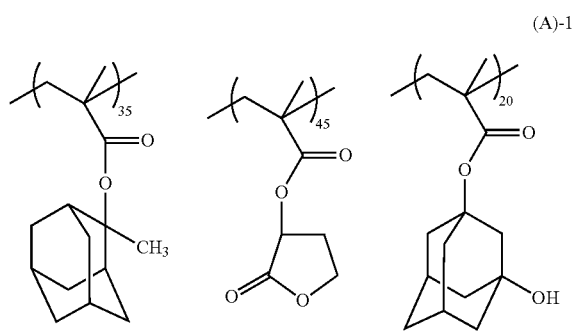

(A)-1

Mw: 7,000, Mw/Mn: 1.8)

Each of the resist compositions prepared with the formulations indicated in Table 1 was applied onto an 8-inch silicon wafer using a spinner, and was then prebaked (PAB) on a hotplate at 110° C. for 60 seconds and dried, thereby forming a resist film having a in thickness of 120 nm.

Subsequently water was dropped onto the surface of the resist film (prior to exposure), and the contact angle (static contact angle) was measured using DROP MASTER-700 (manufactured by Kyowa Interface Science Co. Ltd.) (measurement of contact angle: 2 µL of water). The measured value was defined as the "contact angle after coating (°)".

With respect to the wafer after the measurement of the contact angle, development was peed for 60 seconds at 23° C. in a 2.38% by weight aqueous solution of tetramethylammonium hydroxide (TMAH). Then, the resist film was rinsed for 15 seconds with pure water, and the contact angle was measured in the same manner as described above. The measured value was defined as the "contact angle after development (°)". Further, the difference between the contact angle after coating and the contact angle after development was indicated as "Δ(°)".

The results are shown in Table 2.

TABLE 2

|  | Contact angle after coating (°) | Contact angle after development (°) | Δ (°) |
|---|---|---|---|
| Ex. 6 | 85.6 | 75.9 | −9.7 |
| Ex. 7 | 95.0 | 90.6 | −4.4 |
| Comp. Ex. 1 | 88.3 | 89.7 | 1.4 |
| Comp. Ex. 2 | 68.2 | 59.4 | −8.8 |
| Ex. 8 | 83.3 | 60.0 | −23.3 |
| Ex. 9 | 78.8 | 55.4 | −23.4 |

From the results shown above, it can be seen that in Examples 6 to 9 in which the fluorine-containing compound of the present invention was used and Comparative Example 1 in which the fluorine-containing compound (C)-2 was used, the contact angle after coating was high, as compared to that in Comparative Example 2 in which no fluorine-containing compound was added.

Further, in Examples 6 to 9 in which the fluorine-containing compound of the preset invention was used, the contact angle had been decreased after development. Especially in Examples 8 and 9, the contact angle had been decreased to the same level or lower as that in Comparative Example 2 in which no fluorine-containing compound was added. Therefore, it was confirmed that the resist composition of the present invention was hydrophobic during immersion exposure, and becomes hydrophilic during development. On the other hand, in Comparative Example 1, the protection groups were not dissociated by the developing solution, and hence, the contact angle did not decrease.

Example 10

15 g (84 mmol) of p-hydroxyphenyl methacrylate was added to 150 ml of a THF solution of 11 g (84 mmol) of 3,3,3-trifluoropropionic acid, 19 g (101 mmol) of ethyldiisopropylaminocarbodiimide hydrochloride (EDCl) and 0.5 g (4 mmol) of dimethylaminopyridine (DMAP), in a nitrogen atmosphere at 0° C. Then, the temperature of the reaction liquid was elevated to room temperature, and the reaction liquid was stirred for 3 hours. After conducting thin-layer chromatography to confirm disappearance of the raw materials, the reaction liquid was cooled to 0° C., and water was added to the reaction liquid to terminate the reaction. Thereafter, ethyl acetate was added to the reaction liquid, and extraction was conducted 3 times. Then, the resulting organic phase was washed with water twice. Then, the solvent was distilled off under reduced pressure, and the resulting crude product was purified by recrystallization with heptane/ethyl acetate, thereby obtaining 22 g of a compound (5) represented by formula (5) shown below, in the form of a colorless oily substance (yield: 91%).

[Chemical Formula 55]

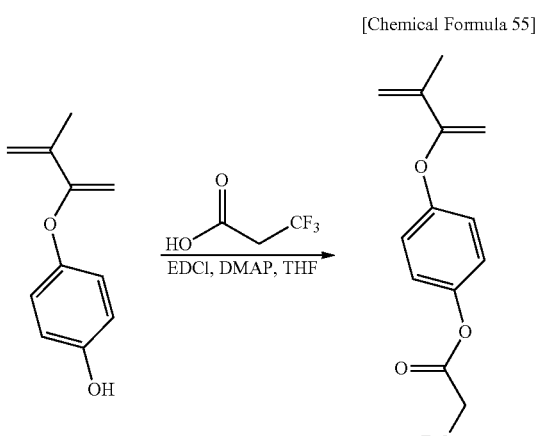

The obtained compound (5) was analyzed by $^1$H-NMR. The results are shown below.

$^1$H-NMR (solvent: DMSO-6d): 7.2-7.1 (m, 4H (H$^c$)), 6.35 (s, 1H (H$^b$)), 5.78 (s, 1H (H$^b$)), 3.46 (m, 2H (H$^d$)), 2.08 (s, 3H (H$^a$)).

From the results shown above, it was confirmed that the compound (5) had a structure shown below.

[Chemical Formula 56]

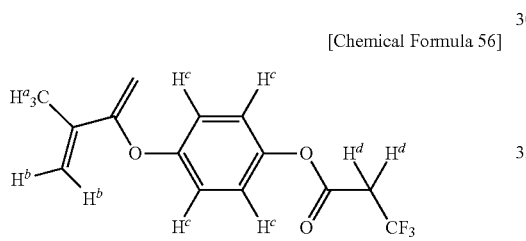

With the exception of using a spreading solvent having a composition of heptane/ethyl acetate=7/3, the same procedure as in Example 1 was performed to confirm that a part of the compound (5) had undergone deprotection (dissociation of —CO—CH$_2$—CF$_3$), and a deprotection product was generated.

Example 11

2.27 g (11.57 mmol) of the compound (5) synthesized in Example 10, 5.00 g (17.36 mmol) of a compound (6) and 41.20 g of THF were charged into a three-necked flask equipped with a thermometer and a reflux tube, and the compounds were dissolved by stirring. Then, 1.74 mmol of a polymerization initiator product name: V-601, manufactured by Wako Pure Chemical Industries, Ltd.) was added and dissolved in the resulting solution, and the solution was subjected to a polymerization reaction in a nitrogen atmosphere at 80° C. for 6 hours while heating and stirring. After the completion of the polymerization reaction, the polymerization reaction liquid was cooled to room temperature. Then, the polymerization reaction liquid was concentrated under reduced pressure, and was dropwise added to an excess amount of n-heptane to perform an operation to deposit a polymer. The deposited polymer was separated by filtration, washed and dried, thereby obtaining 4.50 g of an objective fluorine-containing compound (C)-5.

The obtained compound (C)-5 was analyzed by $^{13}$C-NMR (600 MHz). As a result, it was found that the 1:m ratio in formula (C)-5 shown below was 68.7:31.3 (molar ratio). Further, with respect to (C)-5, the weight average molecular weight and the dispersity were determined by the polystyrene equivalent value as measured by gel permeation chromatography (GPC). As a result, it was found that the weight average molecular weight was 18,600, and the dispersity was 1.84.

[Chemical Formula 57]

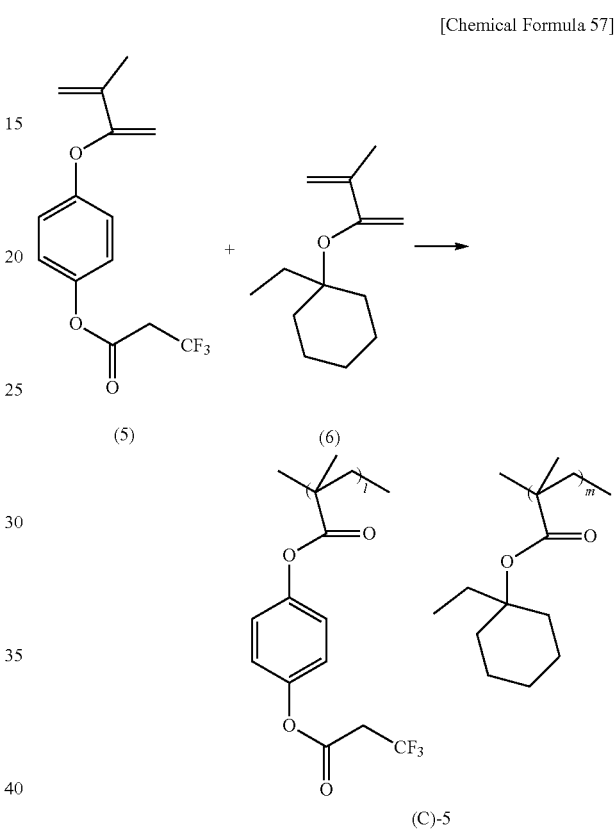

Example 12

The components shown in Table 3 were mixed together and dissolved to obtain a resist composition.

In Table 3, (A)-1, (B)-1, (D)-1 and (S)-1 are the same as in Table 1. Further, in Table 3, (C)-5 indicates the fluorine-containing compound (C)-5 synthesized in Example 11.

TABLE 3

| | Component (A) | Component (B) | Component (C) | Component (D) | Component (S) |
|---|---|---|---|---|---|
| Ex. 12 | (A)-1 [100] | (B)-1 [8.0] | (C)-5 [1.0] | (D)-1 [1.2] | (S)-1 [1500] |

The resist composition of Example 12 was applied onto an 8-inch silicon wafer using a spinner, and was then prebaked (PAB) on a hotplate at 110° C. for 90 seconds and dried, thereby forming a resist film having a film thickness of 120 nm.

Subsequently, water was dropped onto the surface of the resist film (prior to exposure), and the contact angle (static contact angle) was measured using DROP MASTER-700

(manufactured by Kyowa Interface Science Co. Ltd.) (measurement of contact angle: 2 μL of water). The measured value was defined as the "contact angle after coating (°)".

With respect to the wafer after the measurement of the contact angle, development was performed for 30 seconds or 60 seconds at 23° C. in a 2.38% by weight aqueous solution of tetramethylammonium hydroxide (TMAH). Then, the resist film was rinsed for 15 seconds with pure water, and the contact angle was measured in the same manner as described above. The measured values (values measured after 30 seconds development and 60 seconds development) were respectively defined as the "contact angle after 30 seconds development (°)" and "contact angle after 60 seconds development (°)". Further, the difference between the contact angle after coating and the contact angle after development was indicated as "Δ(°)".

The results are shown in Table 4.

TABLE 4

| | Contact angle after coating (°) | Contact angle after 30 seconds development (°) | Δ (°) | Contact angle after 60 seconds development (°) | Δ (°) |
|---|---|---|---|---|---|
| Ex. 12 | 78.9 | 61.1 | −17.8 | 60.5 | −18.4 |

From the results shown above, it can be seen that in Example 12 in which the fluorine-containing compound (C)-5 within the scope of the present invention was added, the contact angles after development had been decreased, as compared to the contact angle after coating. Therefore, it was confirmed that the resist composition of the present invention was hydrophobic during immersion exposure, and becomes hydrophilic during development.

The invention claimed is:

1. A resist composition for immersion exposure comprising a base component (A) which exhibits changed solubility in an alkali developing solution under action of acid, an acid-generator component (B) which generates acid upon irradiation, and a fluorine-containing compound (C) having a group represented by general formula (C-1) shown below

[Chemical Formula 2]

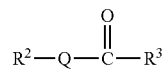
(C-1)

wherein Q represents a group in which one hydrogen atom has been removed from a monovalent hydrophilic group; $R^2$ represents an aromatic cyclic group-containing organic group which may have a fluorine atom, and $R^3$ represents a hydrocarbon group of 2 or more carbon atoms which may have a fluorine atom, with the proviso that at least one of $R^2$ and $R^3$ has a fluorine atom,
wherein the amount of the fluorine-containing compound (C) is 0.1 to 20 parts by weight, relative to 100 parts by weight of the base component (A).

2. The resist composition for immersion exposure according to claim 1, wherein said fluorine-containing compound (C) is at least one compound selected from the group consisting of compounds represented by general formulas (C-1-1) to (C-1-4) shown below:

[Chemical Formula 3]

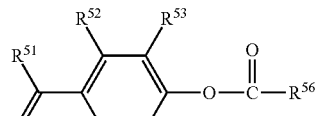
(C-1-1)

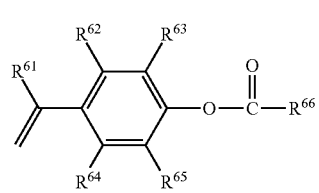
(C-1-2)

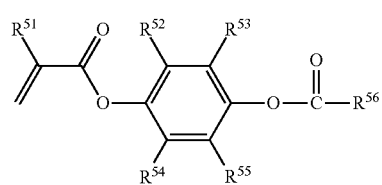
(C-1-3)

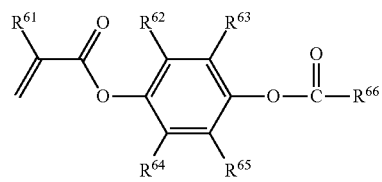
(C-1-4)

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represents a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

3. The resist composition for immersion exposure according to claim 1, wherein said fluorine-containing compound (C) is a polymeric compounds having a structural unit represented by general formula (c1-1-1), (c1-1-2), (c1-1-3) or (c1-1-4) shown below:

[Chemical Formula 4]

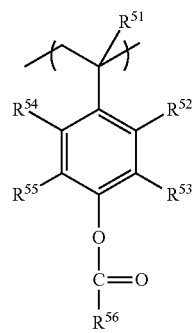
(c1-1-1)

(c1-1-2)

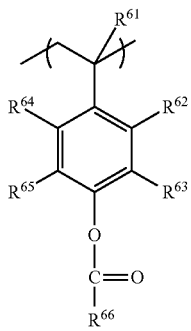

(c1-1-3)

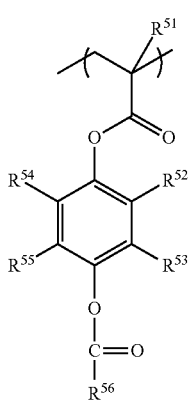

(c1-1-4)

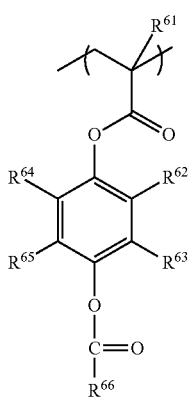

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represents a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

4. The resist composition for immersion exposure according to claim 1, wherein said base component (A) is a base component which exhibits increased solubility in an alkali developing solution under action of acid.

5. The resist composition for immersion exposure according to claim 4, wherein said base component (A) comprises a resin component (A1) which exhibits increased solubility in an alkali developing solution under action of acid, and said resin component (A1) has a structural unit (a1) derived from an acrylate ester containing an acid dissociable, dissolution inhibiting group.

6. The resist composition for immersion exposure according to claim 5, wherein said resin component (A1) further has a structural unit (a2) derived from an acrylate ester containing a lactone-containing cyclic group.

7. The resist composition for immersion exposure according to claim 5, wherein said resin component (A1) further has a structural unit (a3) derived from an acrylate ester containing a polar group-containing aliphatic hydrocarbon group.

8. The resist composition for immersion exposure according to claim 1, which further comprises a nitrogen-containing organic compound (D).

9. A method of forming a resist pattern, comprising: applying a resist composition for immersion exposure of any one of claims 1 to 8 to a substrate to form a resist film on the substrate; subjecting said resist film to immersion exposure; and alkali developing said resist film to form a resist pattern.

10. A fluorine-containing compound comprising at least one compound selected from the group consisting of compounds represented by general formulas (C-1-1) and (C-1-2) shown below:

[Chemical Formula 7]

(C-1-1)

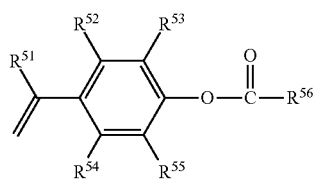

(C-1-2)

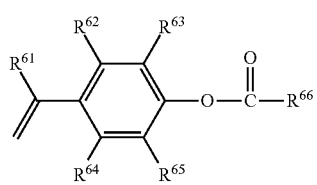

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represents a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

11. A fluorine-containing compound comprising a polymeric compound having a structural unit represented by general formula (c1-1-1) or (c1-1-2) shown below:

[Chemical Formula 8]

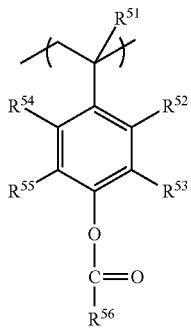

(c1-1-1)

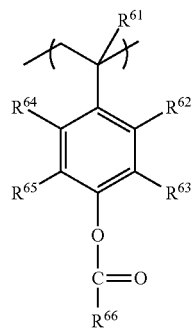

(c1-1-2)

wherein $R^{51}$ represents a hydrogen atom, a lower alkyl group or a halogenated lower alkyl group; each of $R^{52}$ to $R^{55}$ independently represents a hydrogen atom or a fluorine atom, with the proviso that at least one of $R^{52}$ to $R^{55}$ represents a fluorine atom; $R^{56}$ represents a hydrocarbon group of 2 or more carbon atoms which may have a fluorine atom; $R^{61}$ represents a hydrogen atom, a lower alkyl group or a halogenated lower alkyl group; each of $R^{62}$ to $R^{65}$ independently represents a hydrogen atom or a fluorine atom; and $R^{66}$ represents a hydrocarbon group of 2 or more carbon atoms having a fluorine atom.

* * * * *

UNITED STATES PATENT AND TRADEMARK OFFICE
CERTIFICATE OF CORRECTION

| | |
|---|---|
| PATENT NO. | : 7,914,967 B2 |
| APPLICATION NO. | : 12/184566 |
| DATED | : March 29, 2011 |
| INVENTOR(S) | : Sanae Furuya et al. |

It is certified that error appears in the above-identified patent and that said Letters Patent is hereby corrected as shown below:

At Column 1, Line 21, Change "fox" to --for--.

At Column 1, Line 24, Change "though" to --through--.

At Column 1, Line 43, Change "its" to --units--.

At Column 2, Line 17, Change "Pious" to --various--.

At Column 2, Line 66, Change "die" to --the--.

At Column 3, Line 9, Change "van" to --can--.

At Column 3, Line 14, Change "tacking" to --tracking--.

At Column 3, Line 22, After "generated" insert --at--.

At Column 3, Line 30 (Approx.), Change "dug" to --during--.

At Column 5, Line 12, Change "Alternatively" to --Alternatively,--.

At Column 5, Line 14, Change "—NH$_2$." to -- —NH$_2$,--.

At Column 5, Line 31, Change "au" to --all--.

At Column 5, Line 43 (Approx.), Change "all" to --alkyl--.

At Column 6, Line 25, Change "pad" to --part--.

At Column 6, Line 46, Change "trifluromethyl" to --trifluoromethyl--.

At Column 6, Line 66, Change "hereafter," to --(hereafter,--.

At Column 8, Line 43, Change "napthalene" to --naphthalene--.

At Column 8, Line 54, Change "use" to --used--.

At Column 9, Line 34, Change "invention" to --invention,--.

At Column 10, Line 41, Change "represent" to --represents--.

At Column 10, Line 49, Change "cm" to --can--.

At Column 11, Line 10 (Approx.), Change "genera" to --general--.

At Column 11, Line 48 (Approx.), Change "win" to --can--.

Signed and Sealed this
Twenty-seventh Day of September, 2011

David J. Kappos
*Director of the United States Patent and Trademark Office*

CERTIFICATE OF CORRECTION (continued)

U.S. Pat. No. 7,914,967 B2

At Column 12, Line 52, After "other" insert --than--.

At Column 12, Line 60, Change "expose;" to --exposure;--.

At Column 13, Line 10, Change "(Mw/Mm)" to --(Mw/Mn)--.

At Column 13, Line 27, Change "(hereafter" to --(hereafter,--.

At Column 13, Line 43, After "$R^3$" insert --in--.

At Column 14, Line 20, Change "ethydiisopropylaminocarbodiimide" to --ethyldiisopropylaminocarbodiimide--.

At Column 14, Line 23, Change "benzothiazole" to --benzotriazole--.

At Column 15, Line 25, Change "low" to --"low--.

At Column 15, Line 26, Change "compounds)" to --compounds")--.

At Column 15, Line 30, Change "polymer" to --(polymer--.

At Column 15, Line 49, Change "crosslinked" to --cross-linked--.

At Column 15, Line 55, After "in" insert --an--.

At Column 16, Line 10 (Approx.), Change "pas" to --parts--.

At Column 16, Line 43, Change "van" to --can--.

At Column 16, Line 46, Change "acylate" to --acrylate--.

At Column 16, Line 53, Change "a position," to --α-position,--.

At Column 16, Line 55, Change "substituent" to --substituent,--.

At Column 17, Line 31, Change "resist" to --resists--.

At Column 17, Line 37, Change "at" to --that--.

At Column 18, Line 9 (Approx.), Change "at" to --that--.

At Column 18, Line 52-67 (Structure), Change

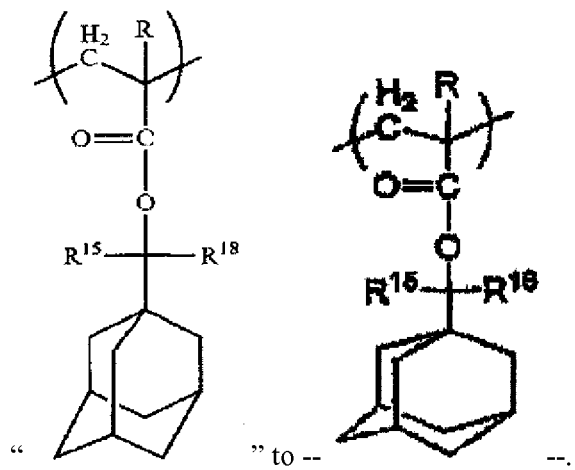

At Column 19, Line 19-30,
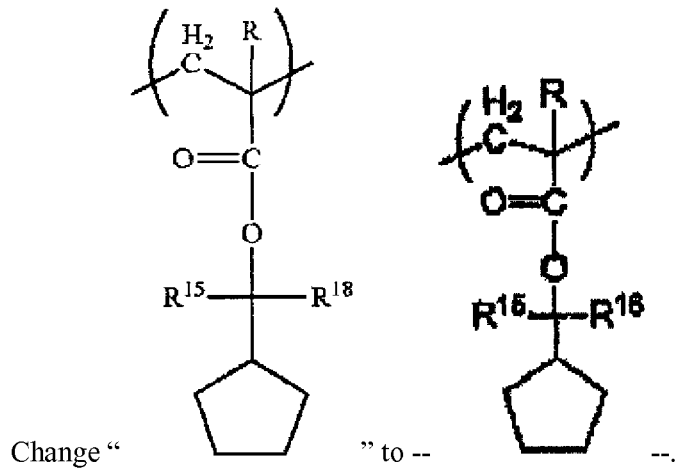
Change " " to -- --.
At Column 20, Line 53, Change "group," to --group;--.
At Column 21, Line 35, Change "teal" to --terminal--.
At Column 21-22, Line 67 (Col. 21) 1 (Col. 22), Change "preferably" to --(preferably--.
At Column 22, Line 29, Change "a" to --an--.
At Column 22, Line 49, Change "a" to --an--.
At Column 24, Line 3-19,
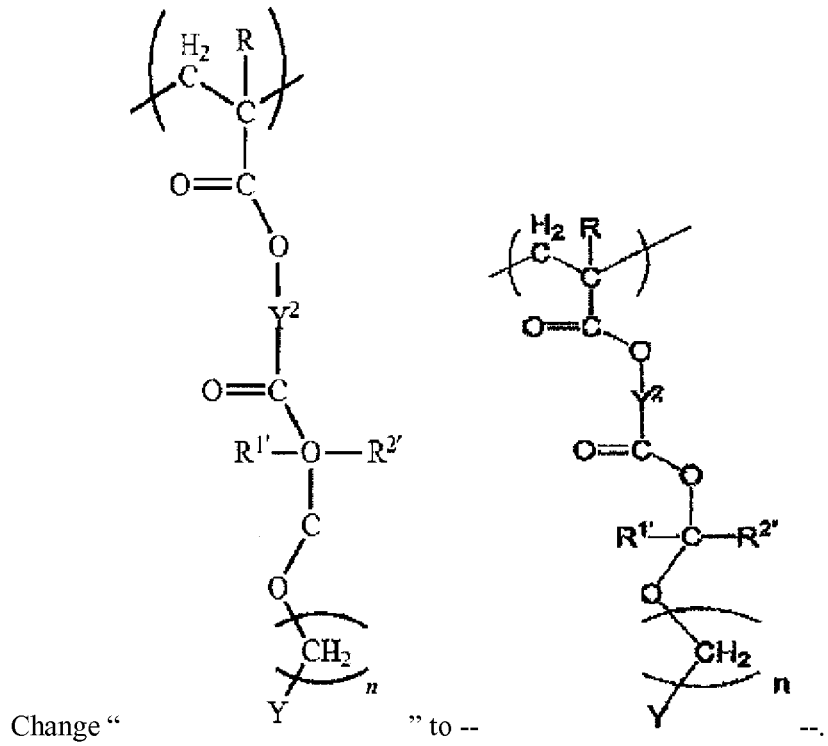
Change " " to -- --.

At Column 25, Line 51-58 (Approx.),

Change " 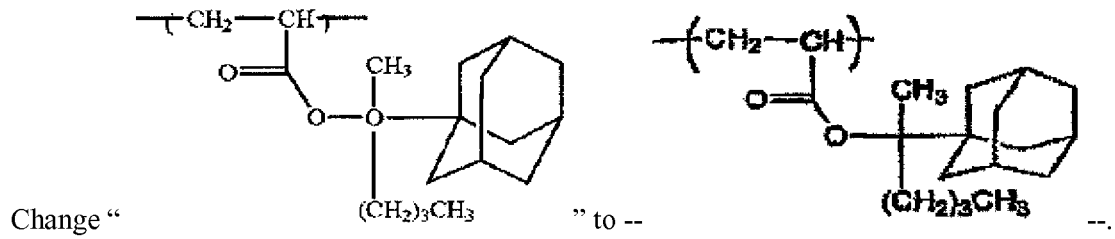 to -- --.

At Column 35, Line 22 (Approx.), Change "(a-1-2-26)" to --(a1-2-26)--.
At Column 36, Line 2 (Approx.), Change "(A1-2-31)" to --(a1-2-31)--.
At Column 36, Line 22 (Approx.), Change "(A1-2-33)" to --(a1-2-33)--.
At Column 51, Line 66, Change " 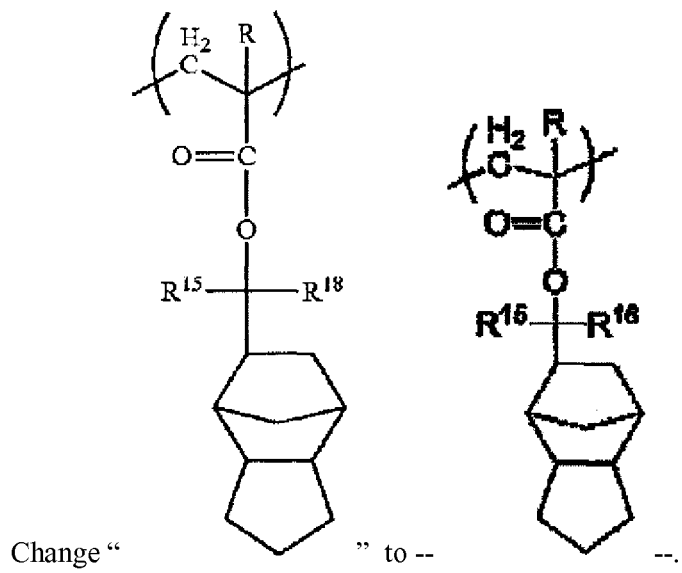 to -- --.

At Column 58, Line 59 (Approx.), Change "(a-1-1-6)" to --(a1-1-6)--.
At Column 59, Line 54, Change "rage," to --range,--.
At Column 61, Line 32 (Approx.), Change "fox" to --for--.
At Column 68, Line 58-59, Change "consisting" to --constituting--.
At Column 68, Line 64, Change "bad," to --hand,--.
At Column 69, Line 46, Change "it" to --unit--.
At Column 71, Line 2, Change "structure" to --structural--.
At Column 71, Line 10, Change "Thom" to --from--.
At Column 72, Line 65, Change "preferably" to --preferable--.
At Column 73, Line 12 (Approx.), Change "it" to --in--.
At Column 73, Line 33 (Approx.), Change "says" to --say,--.

At Column 73, Line 49 (Approx.), Change "sulfon" to --sulfonium--.

At Column 74, Line 10, Change "way" to --may--.

At Column 74, Line 15 (Approx.), Change "$R^{5}$"," to --$R^{5}$"--.

At Column 74, Line 40, Change "substituted" to --substituted,--.

At Column 75, Line 36, Change "substitute" to --substituent,--.

At Column 77, Line 60 (Approx.), Change "n-propanesulfonic," to --n-propanesulfonate,--.

At Column 79, Line 35, Change "different" to --different.--.

At Column 79, Line 50 (Approx.), Change "ad" to --and--.

At Column 80, Line 6 (Approx.), Change "suit" to --sulfur--.

At Column 80, Line 29 (Approx.), Change "at" to --an--.

At Column 80, Line 50, Before "cyano" insert --a--.

At Column 82, Line 29, Change "(n-butylsulfonyloximino)" to --(n-butylsulfonyloxyimino)--.

At Column 82, Line 35, Change "(propylsulfonyloxyimino" to --(propylsulfonyloxyimino)--.

At Column 82, Line 41, Change "oxine" to --oxime--.

At Column 82, Line 42, Change "disclose" to --disclosed--.

At Column 83, Line 21, Change "an" to --and--.

At Column 84, Line 8, After "more" insert --than--.

At Column 84, Line 15, Change "trietylamine," to --triethylamine,--.

At Column 84, Line 39, Change "part" to --parts--.

At Column 84, Line 48, Change "phosphors" to --phosphorus--.

At Column 84, Line 57, Change "abovementioned" to --above-mentioned--.

At Column 85, Line 25, Change "γ-butolactone;" to --γ-butyrolactone;--.

At Column 85, Line 26, Change "acetone;" to --acetone,--.

At Column 86, Line 18, Change "fox" to --for--.

At Column 86, Line 46, Change "(tacking" to --(tracking--.

At Column 86, Line 60, Change "expose" to --exposed--.

At Column 86, Line 64, Change "ad" to --and--.

At Column 87, Line 35, Change "ad" to --and--.

At Column 87, Line 44, Change "dining" to --during--.

At Column 88, Line 3, Change "step" to --state--.

At Column 88, Line 13, Change "inclined" to --inclined,--.

At Column 88, Line 28, Change "Ltd.)" to --Ltd.),--.

At Column 88, Line 41, Change "dog" to --during--.

At Column 88, Line 49, Change "handy" to --hand,--.

CERTIFICATE OF CORRECTION (continued)
U.S. Pat. No. 7,914,967 B2

At Column 89, Line 11 (Approx.), Change "enhance" to --enhanced,--.

At Column 89, Line 32 (Approx.), Change "like;" to --like,--.

At Column 89, Line 55, Change "pattering" to --patterning--.

At Column 89, Line 57, Change "of for" to --of forming--.

At Column 90, Line 6, Change "consist" to --consisting--.

At Column 90, Line 63, Change "my" to --any--.

At Column 92, Line 42, Change "product" to --product:--.

At Column 92, Line 63, Change "(C)-1" to --(C)-1,--.

At Column 94, Line 43 (Approx.), Change "get" to --gel--.

At Column 96, Line 10 (Approx.), Change "fluorine-on" to --fluorine-containing--.

At Column 96, Line 11 (Approx.), Change "result" to --result,--.

At Column 96, Line 15 (Approx.), Change "ratio;" to --ratio:--.

At Column 97, Line 45 (Approx.), Change "Mw:" to --(Mw:--.

At Column 97, Line 51 (Approx.), Change "a in" to --a film--.

At Column 97, Line 52 (Approx.), Change "Subsequently" to --Subsequently,--.

At Column 97, Line 59 (Approx.), Change "peed" to --performed--.

At Column 98, Line 29, Change "preset" to --present--.

At Column 99, Line 55, Change "product" to --(product--.

At Column 101, Line 44 (Approx.), In Claim 1, after "below" insert --:--.